US007361633B2

(12) United States Patent
Maudsley et al.

(10) Patent No.: US 7,361,633 B2
(45) Date of Patent: Apr. 22, 2008

(54) SCREENING METHOD AND ANTI-TUMOR DRUG CANDIDATE OBTAINED THEREFROM

(75) Inventors: Stuart Russell Maudsley, Edinburgh (GB); Robert Peter Millar, Edinburgh (GB)

(73) Assignee: Ardana Bioscience Limited, Edinburgh (GB)

( * ) Notice: Subject to any disclaimer, the term of this patent is extended or adjusted under 35 U.S.C. 154(b) by 192 days.

(21) Appl. No.: 10/494,989

(22) PCT Filed: Jul. 22, 2003

(86) PCT No.: PCT/GB03/03269

§ 371 (c)(1),
(2), (4) Date: Feb. 28, 2005

(87) PCT Pub. No.: WO2004/010146

PCT Pub. Date: Jan. 29, 2004

(65) Prior Publication Data

US 2006/0057649 A1 Mar. 16, 2006

(30) Foreign Application Priority Data

Jul. 22, 2002 (GB) ................................. 0216963.9
May 9, 2003 (GB) ................................. 0310678.8

(51) Int. Cl.
*A01N 37/18* (2006.01)
(52) U.S. Cl. ........................................................ 514/2
(58) Field of Classification Search ...................... None
See application file for complete search history.

(56) References Cited

U.S. PATENT DOCUMENTS

| 4,851,385 | A | | 7/1989 | Roeske |
| 5,772,997 | A | * | 6/1998 | Hudziak et al. ......... 424/130.1 |
| 5,854,004 | A | | 12/1998 | Czernilofsky et al. |
| 2002/0058035 | A1 | * | 5/2002 | Garnick et al. .......... 424/145.1 |

FOREIGN PATENT DOCUMENTS

| JP | 05-255366 A1 | 5/1993 |
| WO | WO 96/25423 | 8/1996 |
| WO | WO 01/68704 | 9/2001 |
| WO | WO 01/74377 | 10/2001 |
| WO | WO 01/78796 | 10/2001 |
| WO | WO 01/81408 | 11/2001 |
| WO | WO 02/00701 | 1/2002 |
| WO | WO 02 00701 A | 1/2002 |
| WO | WO 02/086079 | 10/2002 |
| WO | WO 03/004678 | 1/2003 |
| WO | WO 03/023010 | 3/2003 |

OTHER PUBLICATIONS

Debruyne et al., Future Oncol, 2006, 2:677-696.*
Emons et al., Cancer Res, 1993, 53:5439-5446.*
Gura, Science, 1997, 278:1041-1042.*
Curti, Crit. Rev. in Oncology/Hematology, 1993, 14:29-39.*
Jain, Sci. Am., 1994, 271:58-65.*
Freshney, Culture of Animal Cells, A Manual of Basic Technique, Alan R. Liss, Inc., 1983, New York, p4.*
Dermer, Bio/Technology, 1994, 12:320.*
Zipps et al., In Vivo, 2005, 19:1-7.*
Medline Online Encyclopedia—Endometriosis.*
Miller et al., "A Novel Mammalian Receptor For The Evolutionarily Conserved Type II GnRH," *Proceedings Of The National Academy Of Sciences Of USA, National Academy Of Science*, Washington, US, 98:9636-9641 (2001).
Imai et al., "Coupling Of Gonadotropin-Releasing Hormone Receptor To Gi Protein In Human Reproductive Tract Tumors," *The Journal Of Clinical Endocrinology And Metabolism*, 81:3249-3253 (1996).
Oyesiku et al., "Pituitary Adenomas: Screening For Galphaq Mutations," *Journal Of Clinical Endocrinology And Metabolism*, 82:4184-4188 (1997).
Audinot et al., "Structure-Activity Relationships Studies of Melanin-Concentrating Hormone (MCH)-Related Peptide Ligands at SLC-1, the Human MCH Receptor," *J. Biol. Chem.*, 276:13554-13562 (2001).

(Continued)

*Primary Examiner*—Misook Yu
*Assistant Examiner*—Mark Halvorson
(74) *Attorney, Agent, or Firm*—Nixon Peabody LLP

(57) ABSTRACT

A method for identifying a test compound that has an anti-tumoral effect whilst not significantly activating unrelated transduction signals, the method comprising the steps of: (a) selecting at least one test compound; (b) assaying the compound for anti-tumoral effect; (c) selecting at least one distinct intracellular event which is modulated, at least partially, by the GnRH receptor; (d) testing for the ability of said test compound not to modulate the selected intracellular event; and (e) selecting the test compound which selectively demonstrates an anti-tumoral effect and does not modulate said other selected intracellular event. A method according to any one of the preceding claims, the method comprising: (a) selecting at least one test compound; (b) determining whether the test compound activates signalling via Gαi; (d) testing for the ability of said test compound not to modulate signalling via Gαq; and (e) selecting the test compound which selectively activates signalling via Gαi and does not modulate signalling via Gαq. Compounds selected by the methods, including Ac-D-Nal(2)-D-4-ClPhe-D-Pal-Ser-1-MePal-D-IsopropylLys-Leu-IsopropylLys-Pro-D-AlaNH$_2$, are useful in combating cancer and reproductive tissue hyperplasias.

4 Claims, 24 Drawing Sheets

OTHER PUBLICATIONS

Figure 1:
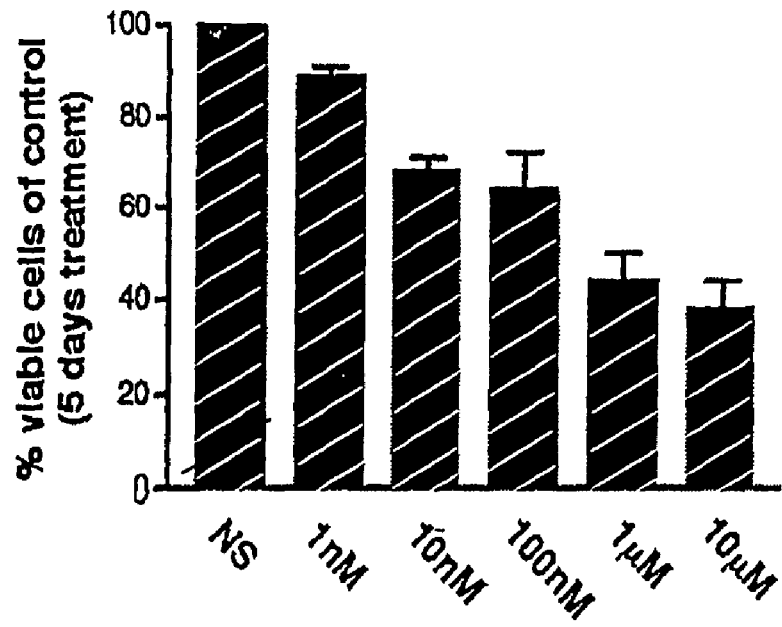
Figure 1:
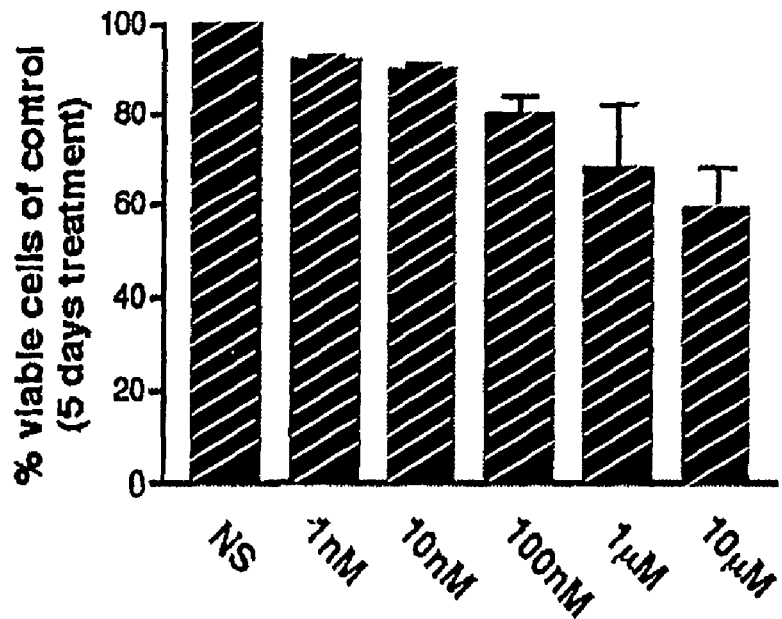
Figure 1:
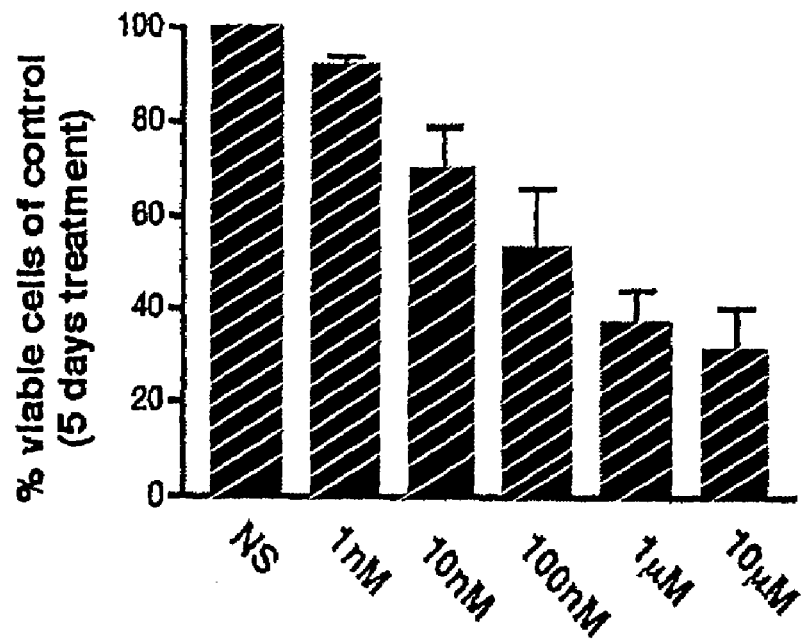
Figure 1:
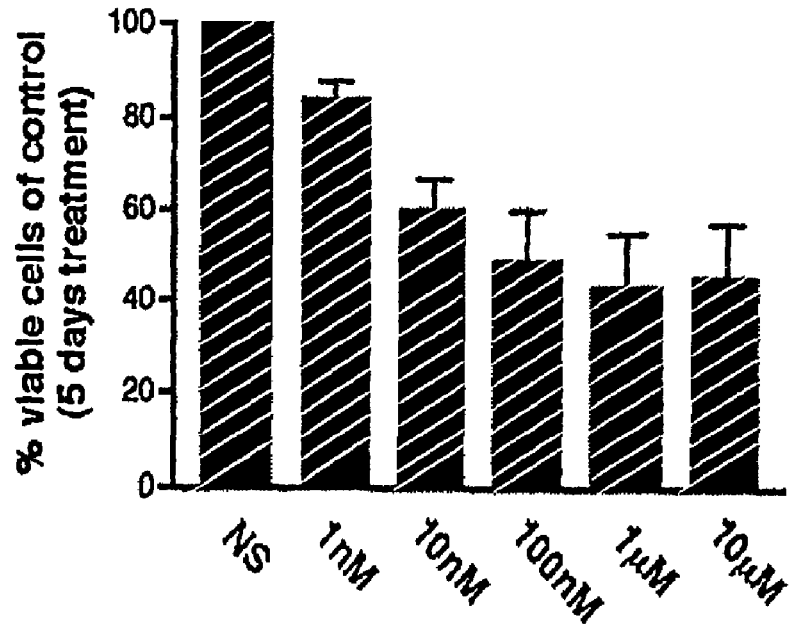

Benard et al., "Role of Dynamin, Src, and Ras in the Protein Kinase C-Mediated Activation of ERK by Gonadotropin-Releasing Hormone," *J. Biol. Chem.*, 276:4554-4563 (2001).

Chatzaki et al., "The Expression of Gonadotropin-Releasing Hormone and its Receptor in Endometrial Cancer, and its Relevance as an Autocrine Growth Factor," *Cancer Res.*, 56:2059-2065 (1996).

Chegini et al., "Gonadotropin-Releasing Hormone (GnRH) and GnRH Receptor Gene Expression in Human Myometrium and Leiomyomata and the Direct Action of GnRH Analogs on Myometrial Smooth Muscle Cells and Interaction with Ovarian Steroids in Vitro," *J. Clin. Endocrinol. Metab.*, 81:3215-3221 (1996).

[Database Accession No. 2004:80979] Maudsley, "Screening Method and Anti-Tumor Drug Candidate Obtained Therefrom," *Chemical Abstracts Service* (2004).

Emons et al., "Growth-Inhibitory Actions of Analogues of Luteinizing Hormone Releasing Hormone on Tumor Cells," *Trends Endocrinol. Metab.*, 8:355-362 (1997).

GenBank Accession No. JQ1042 (2000).

GenBank Accession No. NP_005288 (2003).

Grosse et al., "Gonadotropin-Releasing Hormone Receptor Initiates Multiple Signaling Pathways by Exclusively Coupling to $G_{q/11}$ Proteins," *J. Biol. Chem.*, 275:9193-9200 (2000).

Grundker et al., "Antiproliferative Signaling of Luteinizing Hormone-Releasing Hormone in Human Endometrial and Ovarian Cancer Cells through G Protein $\alpha_i$-Mediated Activation of Phosphotyrosine Phosphatase," *Endocrinology*, 142:2369-2380 (2001).

Grundker et al., "Expression of Gonadotropin-Releasing Hormone II (GnRH-II) Receptor in Human Endometrial and Ovarian Cancer Cells and Effects of GnRH-II on Tumor Cell Proliferation," *J. Clin. Endocrinol. Metab.*, 87:1427-1430 (2002).

Gutkind, "The Pathways Connecting G Protein-Coupled Receptors to the Nucleus through Divergent Mitogen-Activated Protein Kinase Cascades," *J. Biol. Chem.*, 273:1839-1842 (1998).

Halmos et al., "Down-Regulation and Change in Subcellular Distribution of Receptors for Luteinizing Hormone-Releasing Hormone in OV-1063 Human Epithelial Ovarian Cancers During Therapy with LH-RH Antagonist Cetrorelix," *Int. J. Oncology*, 17:367-373 (2000).

Huang et al., "Fas and Its Ligand, Caspases, and Bcl-2 Expression in Gonadotropin-Releasing Hormone Agonist-Treated Uterine Leiomyoma," *J. Clin. Endocrinol. Metab.*, 87:4580-4586 (2002).

Imai and Tamaya, "GnRH Receptor and Apoptotic Signaling," *Vitamins and Hormones*, 59:1-33 (2000).

Imai et al., "Coupling of Gonadotropin-Releasing Hormone Receptor to Gi Protein in Human Reproductive Tract Tumors," *J. Clin. Endocrin. Metabolism*, 81:3249-3253 (1996).

Jungwirth et al., "Inhibition of Growth of Androgen-Independent DU-145 Prostate Cancer In Vivo by Luteinising Hormone-Releasing Hormone Antagonist Cetrorelix and Bombesin Antagonists RC-3940-II and RC-3950-II," *Eur. J. Cancer*, 33:1141-1148 (1997).

Jungwirth et al., "Luteinizing Hormone-Releasing Hormone Antagonist Cetrorelix (SB-75) and Bombesin Antagonist RC-3940-II Inhibit the Growth of Androgen-Independent PC-3 Prostate Cancer in Nude Mice," *Prostate*, 32:164-172 (1987).

Kakar et al., "Inhibition of Growth and Proliferation of EcRG293 Cell Line Expressing High-Affinity Gonadotropin-Releasing Hormone (GnRH) Receptor Under the Control of an Inducible Promoter by GnRH Agonist ($_D$-Lys$^6$)GnRH and Antagonist (Antide)$^1$," *Cancer Research*, 58:4558-4560 (1998).

Kang et al., "Gonadotropin-Releasing Hormone Activates Mitogen-Activated Protein Kinase in Human Ovarian and Placental Cells," *Mol. Cell Endocrinol.*, 170:143-151 (2000).

Kang et al., "Role of Gonadotropin-Releasing Hormone as an Autocrine Growth Factor in Human Ovarian Surface Epithelium," *Endocrinology*, 141:72-80 (2000).

Kenakin et al., "Agonist-Receptor Efficacy II: Agonist Trafficking of Receptor Signals," *Trends Pharmacol. Sciences*, 16:232-238 (1995).

Kimura et al., "Role of Mitogen-Activated Protein Kinase/Extracellular Signal-Regulated Kinase Cascade in Gonadotropin-Releasing Hormone-Induced Growth Inhibition of a Human Ovarian Cancer Cell Line," *Cancer Res.*, 59:5133-5142 (1999).

Korkut et al., "Inhibition of Growth of Experimental Prostate Cancer with Sustained Delivery Systems (Microcapsules and Microgranules) of the Luteinizing Hormone-Releasing Hormone Antagonist SB-75," *Proc. Natl. Acad. Sci. USA*, 88:844-848 (1991).

Kraus et al., "Intracellular Signaling Pathways Mediated by the Gonadotropin-Releasing Hormone (GnRH) Receptor," *Arch. Medical Research*, 32:499-509 (2001).

Leibovitz et al., "Sequential Degradation of the Neuropeptide Gonadotropin-Releasing Hormone by the 20 S Granulosa Cell Proteasomes," *FEBS Lett.*, 346:203-206 (1994).

Mangoura et al., "Prolactin Concurrently Activates Src-PLD and JAK/Stat Signaling Pathways to Induce Proliferation While Promoting Differentiation in Embryonic Astrocytes," *Int. J. Dev. Neurosci.*, 18:693-704 (2000).

McArdle et al., "Signalling, Cycling and Desensitisation of Gonadotropin-Releasing Hormone Receptors," *J. Endocrin.*, 173:1-11 (2002).

McArdle et al., "The Gonadotrophin-Releasing Hormone Receptor: Signalling, Cycling and Desensitisation," *Arch. Physiol. Biochem.*, 110:113-122 (2002).

Millar et al., "A Novel Mammalian Receptor for the Evolutionary Conserved Type II GnRH," *Proc. Natl. Acad. Sci. USA*, 98:9636-9641 (2001).

Ott et al., "Two Mutations in Extracellular Loop 2 of the Human GnRH Receptor Convert and Antagonist to and Agonist," *Mol. Endocrinol.*, 16:1079-1088 (2002).

Oyesiku et al., "Pituitary Adenomas: Screening for G$\alpha$q Mutations," *J. Clin. Endocrin. Metabolism*, 82:4184-4188 (1997).

Ravenna et al., "Effects of Triptorelin, a Gonadotropin-Releasing Hormone Agonist, on the Human Prostatic Cell Lines PC3 and LNCaP," *J. Androl.*, 21:549-557 (2000).

Redding et al., "Sustained Release Formulations of Luteinizing Hormone-Releasing Hormone Antagonist SB-75 Inhibit Proliferation and Enhance Apoptotic Cell Death of Human Prostate Carcinoma (PC-82) in Male Nude Mice," *Cancer Res.*, 52:2538-2544 (1992).

Saito et al., "Effects of GnRH Antagonists on Phorbol Ester-Induced LH Release from Rat Pituitary Gonadotrophs," *Endocrine J.*, 41:415-419 (1994).

Schally et al., "Hypothalamic and Other Peptide Hormones," *Cancer Medicine*, 4th Ed., Baltimore: Williams & Wilkins, pp. 827-840 (1997).

Schally, A. V., "Luteinizing Hormone-Releasing Hormone Analogs: Their Impact on the Control of Tumorgenesis," *Peptides*, 20:1247-1262 (1999).

Sun et al., "A Chicken Gonadotropin-Releasing Hormone Receptor That Confers Agonist Activity to Mammalian Antagonists," *J. Biol. Chem.*, 276:7754-7761 (2001).

Tang et al., "Cellular Mechanisms of Growth Inhibition of Human Epithelial Ovarian Cancer Cell Line by LH-Releasing Hormone Antagonist Cetrorelix," *J. Clin. Endocrin.*, 87:3721-3727 (2002).

Yamaguchi et al., "Regulated Interaction of Endothelin B Receptor with Caveolin-1," *Eur. J. Biochem.*, 270:1816-1827 (2003).

Yin et al., "Expression of the Messneger RNA for Gonadotropin-Releasing Hormone and its Receptor in Human Cancer Cell Lines," *Life Sci.*, 62:2015-2023 (1998).

Bonfil et al., "Role of Map-Kinase (MAPK) in GnRH-Stimulated Transcriptional Regulation of Gonadotropin Subunit Genes," 7th *International Symposium of GnRH Analogues in Cancer and Human Reproduction*, Amsterdam (Feb. 2003) (abstract).

Millar et al., "Mechanism of Anti-Proliferative and Apoptotic Effects of GnRH Agonists and Antagonists in Hormone Dependent Cancer Cell Lines," 7th *International Symposium of GnRH Analogues in Cancer and Human Reproduction*, Amsterdam (Feb. 2003) (abstract).

Tavtigian et al., "Prostate Cancer Susceptibility Genes," 7th *International Symposium of GnRH Analogues in Cancer and Human Reproduction*, Amsterdam (Feb. 2003) (abstract).

Millar et al., "Molecular Mechanisms of GnRH Receptor Activation," 7th *International Symposium of GnRH Analogues in Cancer and Human Reproduction*, Amsterdam (Feb. 2003) (abstract).

Limonta et al. Endocrinology 140(11):5250-5256 (1999).

* cited by examiner

SCREENING METHOD AND ANTI-TUMOR DRUG CANDIDATE OBTAINED THEREFROM

This application is a national stage application under 35 U.S.C. § 371 from PCT Application No. PCT/GB2003/003269 filed Jul. 22, 2003, which claims the priority benefit of Great Britain Application No. 0216963.9 filed Jul. 22, 2002 and Great Britain Application No. 0310678.8 filed May 9, 2003.

The invention relates to a new screening method for selecting an active compound useful for the treatment of cancer or reproductive tissue hyperplasia.

GnRH (Gonadotropin-Releasing Hormone) is a decapeptide which plays a pivotal role in the control of the reproductive axis of most known species. It is released in a pulsatile manner from the hypothalamus and acts upon specific receptors in the anterior pituitary controlling the release of luteinizing hormone (LH) and follicle-stimulating hormone (FSH). These two hormones are primary controllers of reproductive function.

A second form of GnRH, GnRH-II has been identified, in the mid-brain of many vertebrates. As a consequence the original form of GnRH has been re-named GnRH I.

GnRH receptor expression has been demonstrated to be a vital component in an autoregulatory cell proliferation process in a number of human malignant tumours, e.g. breast, ovary and endometrial cancers. Several investigations have demonstrated some GnRH-receptor interacting ligands (agonists and antagonists) exert a dose-dependent anti-proliferative effect upon cell lines derived from reproductive tumours. Unlike GnRH receptors in the anterior pituitary, the activation of these peripheral receptors in reproductive tissues activates distinct signalling modalities and seems to respond positively to both classical antagonists and agonists. Despite the differences in cell signalling behaviour, the cloned sequences of the peripheral GnRH receptors appear identical to that of the pituitary GnRH receptor. Therefore a method of selecting novel GnRH receptor ligands which specifically activate the tumour-specific transduction pathways in cancerous tissue, as opposed to those activated by GnRH in the pituitary, would be highly desirable. Such method would allow the selection of ligands of the GnRH receptor having enhanced selectivity and additionally reduce any side effects induced by GnRH treatment since we believe that current GnRH receptor based therapeutics may be less than optimal by inducing tumour progression from benign to more malignant steroid-independent phenotypes. Hence, traditional GnRH receptor based anti-tumour agents act primarily by reducing serum levels of steroids, thus reducing the steroid-dependent growth of the reproductive tumour. Protracted treatment using the classical GnRH receptor-based therapeutics may initially induce regression of the tumour but eventually encourage the growth of more aggressive forms of the tumour.

GnRH agonists are extensively employed in the treatment of sex hormone dependent cancers. The predominant mode of action is believed to be via the desensitization of pituitary gonadotropes. However, a substantial body of evidence points to a direct inhibitory effect of GnRH analogues on these cancer cells. These effects appear to be mediated via the Gαi G-protein in contrast to the predominant Gαq coupling in gonadotropes. Unlike Gαq coupling, Gαi coupling can be activated by both agonists and antagonists. This suggested to us that the receptor involved in the cancer cells may not be the gonadotrope Type I GnRH receptor. The identification of a Type II GnRH receptor in the marmoset which can be activated by both GnRH agonists and certain antagonists suggested that this receptor may be the mediator of anti-proliferative effects in cancer cells. However, extensive attempts to identify this receptor in man have been unable to demonstrate the existence of a conventional Type II receptor transcript which would translate to a full-length functional receptor. The only full-length transcripts present in cancer cells encode the Type I GnRH receptor. We have concluded, therefore, that the different pharmacology (activity of agonists and certain antagonists) of anti-proliferative effects are due to differences in the pharmacology of activation of the Type I receptors when coupled to different intracellular signalling pathways (e.g. via Gαi). We report here detailed studies on the molecular pathways mediating anti-proliferation and apoptosis in reproductive tract cancer cells, in benign hyperplastic cells and in HEK293 cells stably expressing the Type I GnRH receptor. These surprising results indicate for the first time that it is possible to identify compounds which act via the Type I GnRH receptor and which are anti-proliferative in tumour and hyperplastic cells but which at the same time have substantially no effect on the Type I GnRH receptor-mediated pathways of the type found in the pituitary, such as PLCβ activation. Without being bound by any theory, we believe that these compounds stabilise the active form of the GnRH receptor that couples to Gαi rather than Gαq; in other words, we believe that there is differential coupling Gαi and Gαq by the GnRH receptor and that the compounds affect the Gαi-mediated pathway and not the Gαq-mediated pathway.

It is therefore an object of the invention to provide a method for identifying a test compound, preferably a GnRH receptor ligand, that has an anti-tumoral effect whilst not significantly activating unrelated transduction signals, such as the Gαq-PLC-β cascade, which occur in the pituitary. In a first aspect, the method comprises the steps of:

a) selecting at least one test compound, which is preferably a Type I GnRH receptor ligand;
b) assaying the compound for anti-tumoral effect;
c) selecting at least one distinct intracellular event which is modulated, at least partially, by the GnRH receptor;
d) testing for the ability of said test compound not to modulate the selected intracellular event; and
e) selecting the test compound which selectively demonstrate an anti-tumoral effect and does not modulate at least said selected intracellular event.

This method allows the distinction at an early stage, and in vitro, between test compounds which have potential as anti-tumoral compounds, but which activate unwanted transduction signals and, as such, should be disregarded, and it allows the identification of test compounds which are signal-specific and have a greater potential as a therapeutic agent.

Whilst the method can be used to distinguish between already known GnRH agonists/antagonists it can also be used to test other compounds. In this case the method of the invention can advantageously comprise a preliminary step wherein the test compound is tested for its capacity to bind to, and/or modulate the GnRH receptor. Advantageously, compounds which exhibit a high affinity for binding the GnRH receptor are used in the assay method of the invention. Typically, the compound has a $K_D$ for binding the GnRH receptor of between 0.1 and 10 nM, such as about 1 nM. Whether or not a test compound binds to the GnRH receptor can be determined using methods well known in the art, such as a competitive radioligand binding assay. The test compound may be any compound, but typically it is an organic compound of between 100 and 10000 Daltons, preferably between 500 and 5000 Daltons. Typically, the test compound is a compound in a library of test compounds, such as those made using combinatorial chemistry techniques. Also, typically, the test compound is a GnRH analogue.

It will be appreciated that in the methods described herein, which may be drug screening methods, a term well known to those skilled in the art, the selected test compound may be a drug-like compound or lead compound for the development of a drug-like compound.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 15000 daltons and which may be water-soluble. A drug-like compound may additionally exhibit features of bioavailability.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

The assay for anti-tumoral effects in step (b) of the method of the first aspect of the invention can be any one already used in the art for assessing the anti-tumoral activity of GnRH ligands. For example, as described below, the ligands may be assessed for their anti-proliferative effect on choriocarcinoma cell culture. It will be appreciated that the anti-tumoral activity of the compound may also be readily assessed by determining whether the test compound is able to activate a Type I GnRH receptor tumour-specific transduction pathway which leads to an anti-proliferative effect. Typically, cells may be treated with the ligand, and its effect upon cell growth may be measured as the ability to retard numerical cell growth over a period of, for example, 5 days. Viable cells only will be counted, eg by counting those cells which can efficiently exclude Trypan Blue dye.

In a preferred embodiment of the invention, the anti-tumoral effect is assayed by determining whether the test compound activates GnRH receptor-mediated signalling via G$\alpha$i. G$\alpha$i is a heterotrimeric guanine nucleotide binding protein. Typically, it inhibits the enzyme adenylate cyclase. Also included by the term G$\alpha$i any member of the G$\alpha$i subfamily, including G$\alpha$o which is primarily found in the central nervous system. Whether or not a test compound activates GnRH receptor-mediated signalling via G$\alpha$i can be determined by methods well known in the art. For example, and as described in more detail in Example 1, this can be done by determining whether the test compound is able to antagonize forskolin (FSK) stimulated intracellular cAMP accumulation in a suitable cell (such as one which has sufficient G$\alpha$i and adenylate cyclase present to facilitate experimentation) transfected with the Type I GnRH receptor. Thus, in one embodiment, cells (eg human embryonic kidney (HEK) cells) stably expressing Type I GnRH receptor are pre-incubated with test compound then stimulated with forskolin, and cAMP is measured colorimetrically. This is compared with the amount of cAMP produced when equivalent cells are treated with forskolin but not test compound. There is a reduction in cAMP levels in those cells where the test compound is one which is able to activate G$\alpha$i. G$\alpha$i activation may also be measured by its direct association with the receptor, but this is less preferred compared to methods that measure turnover (eg cAMP production). The involvement of G$\alpha$i in a signal transduction event can be assessed using pertussis toxin which inactivates G$\alpha$i; in other words, G$\alpha$i mediated signalling events are pertussis toxin sensitive.

Figure 7:
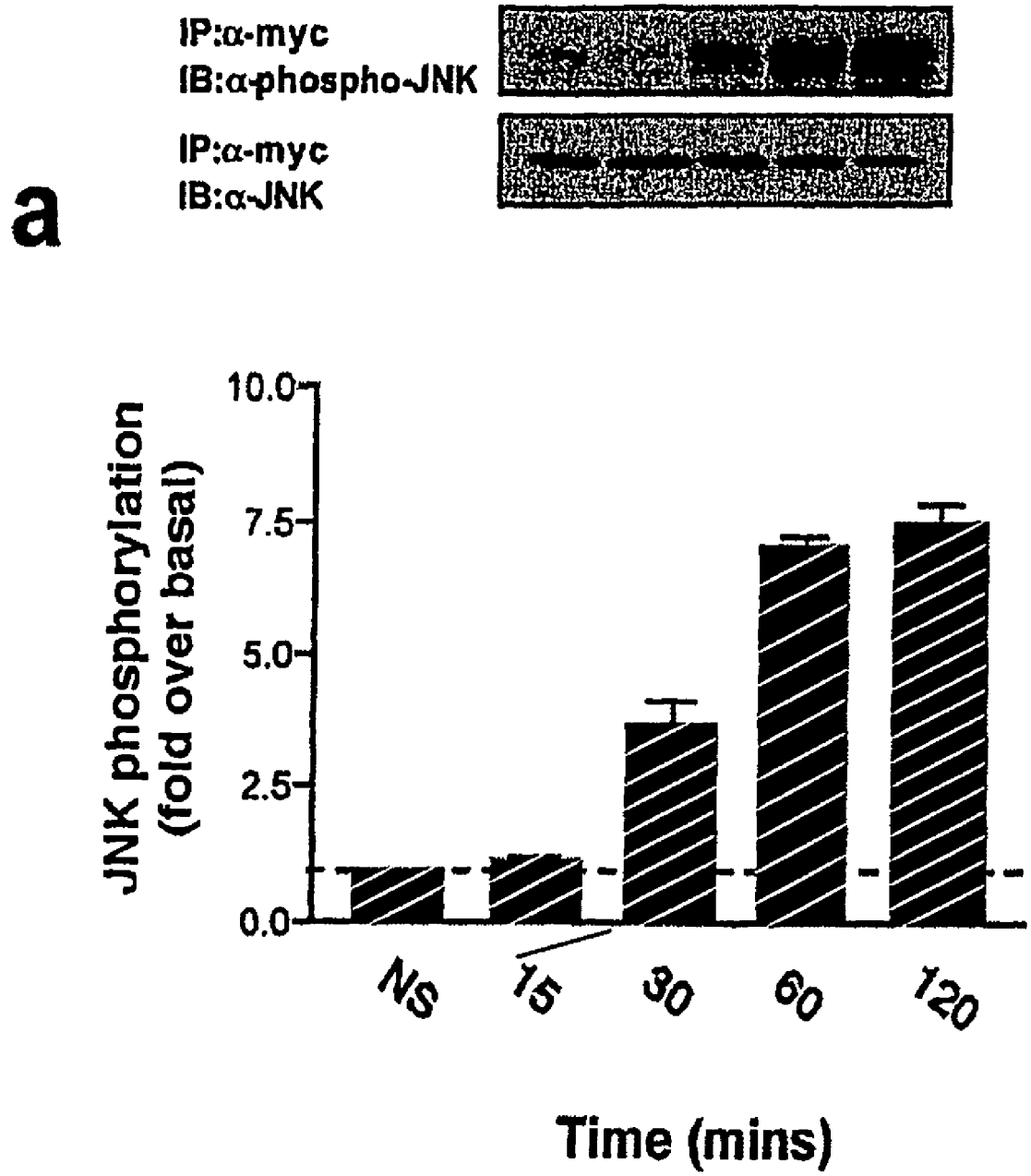
Figure 7:
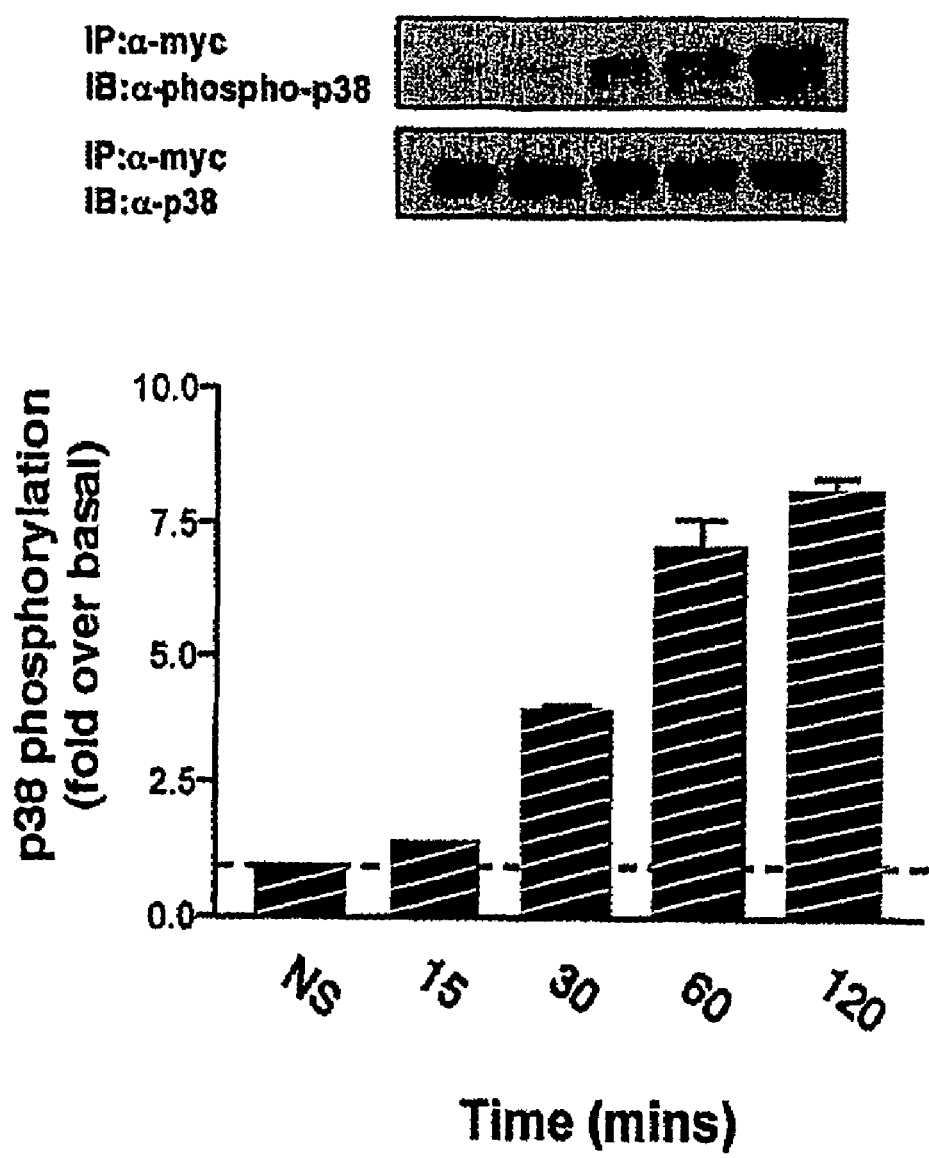
Figure 8:
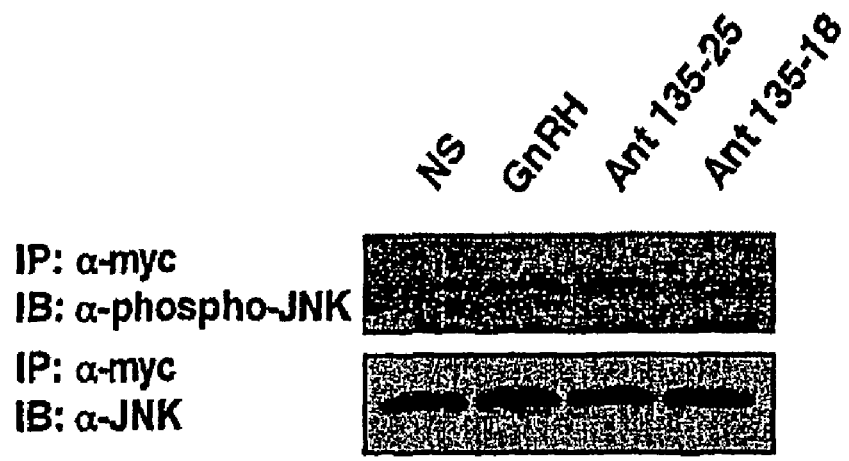
Figure 8:
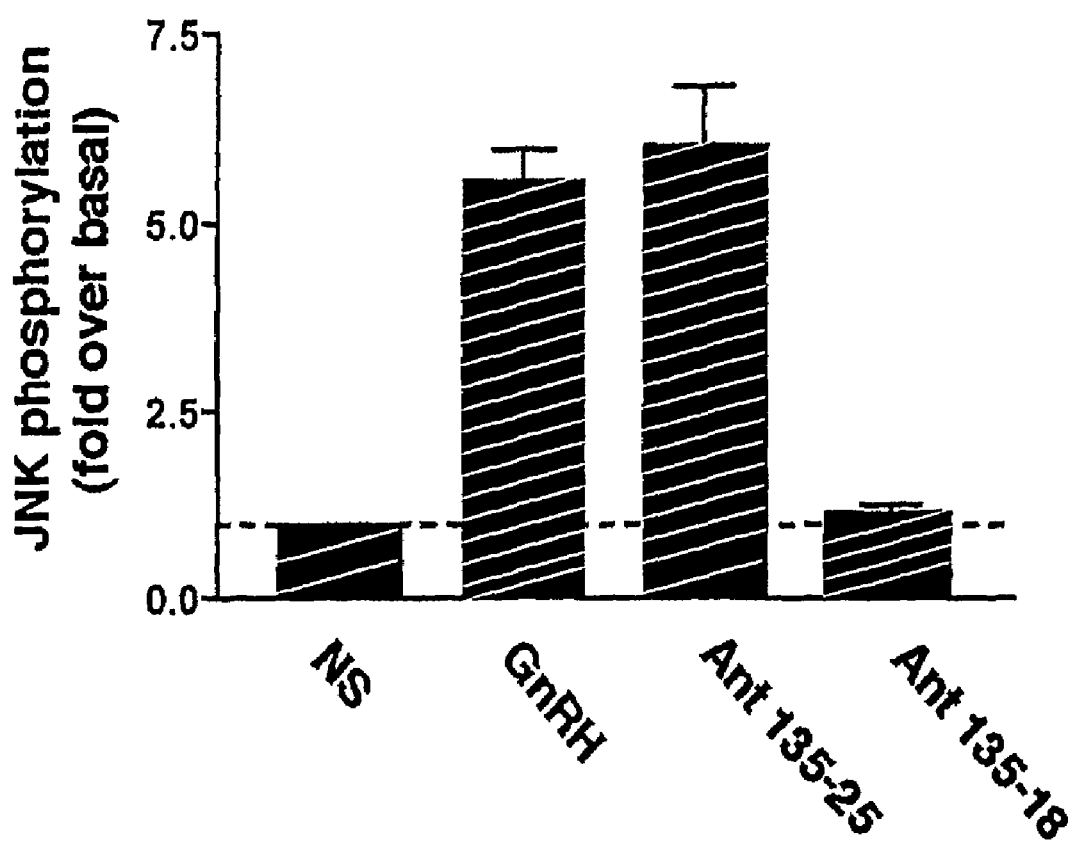
Figure 8:
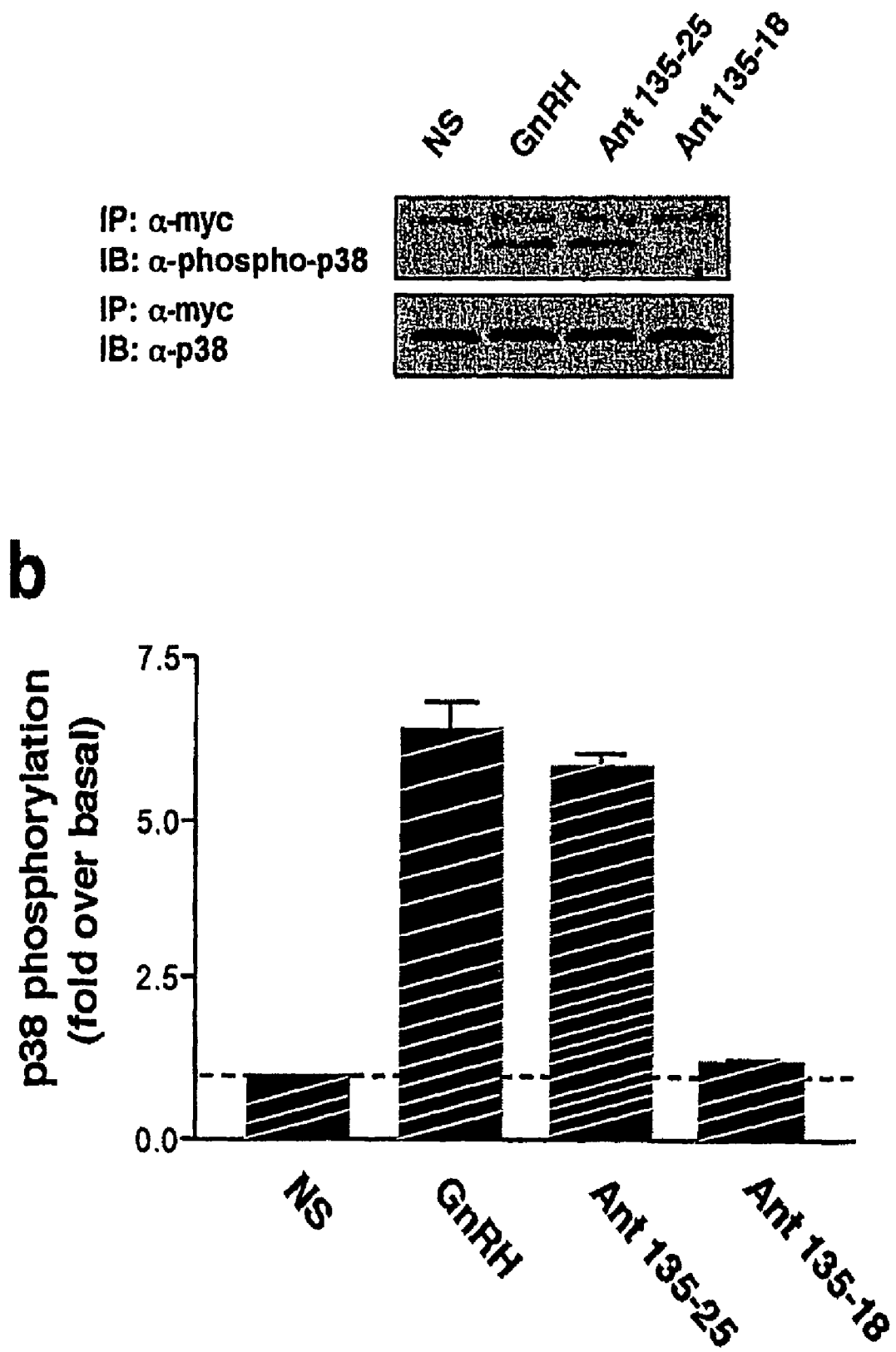

JNK and/or p38$\alpha$ phosphorylation may also be used as a marker of anti-tumoral effect, and G$\alpha$i signalling, and so can be used to assay the effect of the test compounds (see, Example 1, and legend to FIGS. 7 and 8). Similarly, a pertussin toxin (PTX)-sensitive ERK assay may also be used for example using similar methodology as described in relation to JNK and p38$\alpha$ phosphorylation (eg using antibodies selective for phosphorylated ERK1). Typically, cells are pre-incubated with 200 ng/ml PTX for 16 hours before stimulation. The stimulation period is generally 4 to 5 mins. It is particularly preferred if test compounds are selected which are able to produce a 2-fold or greater increase in Erk1/2 phosphorylation above basal in a benign prostate hyperplastic cell.

In addition, it has been evidenced that GnRH ligands can induce a pro-apopotic phenotype in tumour cells, and this may be another way of assessing the anti-tumoral effect of a compound, albeit indirectly. Therefore the method may advantageously comprise the step of assaying the GnRH ligand for the ability to induce a pro-apoptotic state in cultured cells. In particular, determining whether or not a test compound has a pro-apoptotic effect may be useful in connection with other means of assessing the anti-tumoral effect, since this assay provides a strong indication if a test compound is drug-like in vivo. In the Example 1 the extracellular expression of phosphatidylserine (PS) phospholipid was the cellular event chosen as indicative of cellular apoptosis. Extracellular expression of PS can be readily determined making use of labelled (eg fluorescently labelled) Annexin V which selectively binds PS. Measurement of caspase or procaspase may be useful in determining whether or not a test compound is proapoptotic. Such measurments can be carried out in a high throughput screening format with appropriate enzyme substrates.

It will be appreciated that more than one method may be used to assess whether the test compound has an anti-tumoral effect, and it may be advantageous for more than one such method to be used. For example, the capability of a test compound to activate G$\alpha$i may be measured using the cAMP accumulation assay described above, as well as the capability of the test compound to induce a pro-apoptotic state in cultured cells, for example by measuring extracellular expression of PS by Annexin V binding.

Preferably, in step (c), the at least one distinct intracellular event which is modulated, at least partially, by the GnRH receptor is activation of the Type I GnRH receptor pathway which is activated in pituitary (the majority of pituitary function is G$\alpha$q mediated). Preferably, the distinct intracellular event is activation of the G$\alpha$q signalling pathway. G$\alpha$q is a guanine nucleotide binding protein that specifcally activates the enzyme phospholipase C$\beta$. By G$\alpha$q we include G$\alpha$11 and G$\alpha$16, both of which can substitute for G$\alpha$q in various cellular ackgrounds for the activation of phospholipase C$\beta$. In step (d) the test compounds are tested for their ability not to modulate the selected intracellular event (eg the G$\alpha$q signalling pathway) using methods well known in the art. For example, as described in Example 1, activation of the G$\alpha$q signalling pathway may be determined by measuring inositol phosphate production mediated by phospholipase C$\beta$ (PLC$\beta$) production (following Type I GnRH receptor-mediated activation of Gαq). PLCβ is inhibited by U73122 (available from Calbiochem Corporation, CA, USA).

At high levels of receptor stimulation, Gαi can cause PLCβ activation, therefore to show that PLCβ activation is via Gαq and not Gαi, PIX is used to inhibit Gαi, hence PTX-resistant inositol phosphate generation is indicative of Gαq-mediated activation of PLCβ activation. Thus, selecting compounds that do not activate Gαq may readily be done.

In step (e), those test compounds which selectively demonstrate an anti-tumoral effect and do not modulate at least said selected intracellular event are selected for further study. It is particularly preferred if compounds are selected which selectively activate signalling via Gαi and does not modulate signalling via Gαq.

By "anti-tumoral effect" we mean an observable and/or measurable effect. When activation of GnRH receptor-mediated signalling via Gαi is used to assess the anti-tumoral effect, an observable and/or measurable effect may be of downstream events as described herein. When induction of a pro-apoptotic state in cultured cells is used to assess the anti-tumoral effect, an observable and/or measurable effect may be of downstream events as described herein, including the measurement of PS on the surface of dying cells, for example using annexin binding.

If JNK and/or p38α phosphorylation is used as a marker, an observable and measurable effect includes the use of fluorescent radioimmunoassay plate assays, or expression in cells of a marker gene, such as luciferase, whose expression is controlled at least in part by JNK and/or p38α-responsive reporter elements.

By "not modulating at least said selected intracellular event" we mean that the test compound does not substantially modulate said event. It will be appreciated that a test compound may have an effect on the said event but that the effect is not substantial in the context of the invention. For example, if the selected intracellular event is activation of the Gαq signalling pathway, the test compound that is selected for further study is one which does not substantially activate this pathway. It is particularly preferred if the test compound selected is one which is an antagonist of a Type I receptor-mediated Gαq signalling event. It is particularly preferred, however, that the test compound is one with a high efficacy for activation of the Gαi pathway.

In a particular preferred embodiment of the invention, test compounds are selected that have a high potency as an agonist of Gαi stimulation, with the compound having a low potency for Gαq stimulation. Thus, for example, in relation to the given cell proliferation (mediated by Gαi stimulation) or upon PTX-insensitive activation of PLC-β (mediated by Gαq), the following table is helpful in understanding the selection of a test compound with the desirable properties.

| Agonist potency - Gαi | Agonist potency - Gαq |
|---|---|
| Agent A HIGH | Agent Y HIGH |
| Agent B | Agent X |
| Agent C | Agent Z |
| Agent Z | Agent A |
| Agent Y | Agent C |
| Agent X LOW | Agent B LOW |

The most desirable agent would be Agent B since it has a high Gαi potency with the lowest potency at stimulating Gαq.

It will be appreciated that the test compounds selected are ones that are not agonists of a Type I receptor-mediated Gαq signalling event, or only have neligible capacity to activate Gαq pathways. For example, although GnRH I displays the capacity to attenuate cell growth, it possesses the disadvantage of being able to cause gonadotropin secretion from the pituitary (ie is an agonist of a Type I receptor-mediated Gαq signalling event). It will be appreciated, therefore, that the test compounds selected behave like GnRH I at the peripheral tumour site but not like GnRH I at the pituitary level.

Test compounds which are selected in the method typically are those which exhibit a high ratio of Gαq $EC_{50}$/Gα$_i$ $EC_{50}$. $EC_{50}$ means the concentration of test compound which leads to 50% of the maximal response of Gαq or Gαi activation. The smaller the $EC_{50}$ the higher the potency. It is preferred if test compounds with a Gαq $EC_{50}$/Gαi $EC_{50}$ ratio of >10 are selected; more preferably those with a ratio a >50 are selected.

In a preferred aspect, the invention includes a method for selecting a test compound as a potential therapeutic agent or a drug-like compound or a lead compound, the method comprising the steps of:

(a) determining whether the test compound activates GnRH receptor-mediated signalling via Gαi;

(b) determining whether the test compound activates GnRH receptor-mediated signalling via Gαq; and (c) selecting the test compound which selectively activates signalling via Gαi and does not activate signalling via Gαq.

It will be appreciated that by "does not activate signalling via Gαq" we mean does not significantly activate signalling via Gαq. Thus, the test compound selected is one which has a negligible activity to activate Gαq pathways. Preferably, the method is used to select test compounds which are suitable for treating cancer or hyperplasia of reproductive tissue, or are at least drug-like compounds or lead compounds for these indications. The method or assay of the invention may also be used as a research tool to study and define the different activation states of GnRH receptors and pinpoint the biological pathway triggered by a specific state. This, in turn, has important and obvious medical implications for drug design, especially for selecting candidate compounds which do not trigger undesirable side effects.

In a particularly preferred embodiment, assaying the compound for anti-tumoral effect (eg by determining whether the test compound activates GnRH receptor-mediated signalling via Gαi) and testing for the ability of said test compound not to modulate the selected intracellular event (eg determining whether the test compound activates GnRH receptor-mediated signalling via Gαq or not) can be carried out simultaneously on the same cell line using the above-mentioned methods. Typically, a number of cells would be divided between several growth plates and parallel Gαi (eg inhibition of forskolin-induced cAMP accumulation) and Gαq (PLCβ activation) assays are performed simultaneously. Advantageously, the method is one which can be used in high throughput screening systems, for example both of the aforementioned assays can be performed in commercially available radioimmunoassay-based multiwell plate formats.

It will be appreciated that test compounds selected by the method may further be tested for their anti-tumoral effect in model systems such as animal model systems. Test compounds may still further be tested for efficacy in treating reproductive tumours or hyperplasias in clinical trials.

Additionally or alternatively, the test compounds may be used as the drug-like compound or lead compound which is the basis for further drug design.

In a further embodiment the test compound is synthesised and may be packaged and presented as a medicament and/or prepared into a pharmaceutical composition.

The GnRH receptor ligands selected according to the method of the invention are also an object of the invention.

It will be appreciated that preferred compounds selected using the method of the invention are ones which (a) binds a GnRH receptor and (b) selectively activates signalling via Gαi and does not activate signalling via Gαq. It is also preferred if the compounds selected are ones which are GnRH receptor interacting agents which inhibit GnRH-mediated (via Gαq activation) gonadotropin release from the pituitary and directly affect tumour cell growth, in particular in non-steroid resistant tumours.

The ligand 135-25 having the formula: Ac-D-Nal(2)-D-4-ClPhe-D-Pal-Ser-1-MePal-D-IsopropylLys-Leu-IsopropylLys-Pro-D-AlaNH$_2$ (wherein (Mepal is 1-Methyl-3-[3'-pyridyl]-alanine) has shown in vitro potent and selective anti-tumoral activity and has been selected according to the method of the invention. Thus ligand 135-25 (also called Ant 135-25 below), its use in a pharmaceutical composition and especially in the manufacture of a drug for the treatment of tumours, sex-hormone dependent cancer or reproductive tissue hyperplasia is another object of the invention.

Thus, a further aspect of the invention provides a compound selected by the method of the invention for use as a medicament. Suitably, the compound is packaged and presented for use as a medicament, for example with suitable instructions for its use in a patient.

A still further aspect of the invention provides a pharmaceutical composition or formulation comprising a compound selected by the method of the invention, and a pharmaceutically acceptable carrier. The carrier(s) must be "acceptable" in the sense of being compatible with the compound of the invention and not deleterious to the recipients thereof. Typically, the carriers will be water or saline which will be sterile and pyrogen free.

Preferably, the formulation is a unit dosage containing a daily dose or unit, daily sub-dose or an appropriate fraction thereof, of the active ingredient.

A further object is a method of treatment of tumour, sex-hormone dependent cancer or reproductive tissue hyperplasia, such method comprising the step of administering an effective amount of ligand 135-25 to a patient or other compounds selected according to the method of the invention.

In addition, from the work described herein it is shown that compounds, such as 135-25, which bind a GnRH receptor and which selectively activate signalling via Gαi and do not activate signalling via Gαq are useful in treating these diseases. In particular, the compound is also one that has the ability to produce (at a concentration where it has its maximal effect) a 2-fold or greater increase in Erk1/2 phosphorylation over basal in a benign prostate hyperplastic cell such as a BPH-1 cell as described in FIG. 5, Example 1. Typically, the 2-fold or greater increase in Erk1/2 phosphorylation over basal is measured in cells which have been pretreated with PTX as described above (ie using a 16 h pre-incubation with 200 ng/ml PTX before application of the compound).

Thus, a further aspect of the invention provides a method of combating tumours or reproductive tissue hyperplasias of including specifcally uterine fibroids in a patient, the method comprising administering a compound selected according to the invention or a compound which (a) binds a GnRH receptor; (b) selectively activates signalling via Gαi and does not activate signalling via Gαq; and (c) produces a 2-fold or greater increase in Erk1/2 phosphorylation over basal levels in a benign prostate hyperplastic cell.

Preferably, the compound is able to produce a fold-increase in Erk1/2 phosphorylation in benign hyperplastic cells very similar to that produced by GnRH I. Preferably, the compound is 135-25.

The method has uses in both veterinary or human medicine, therefore the patient may be an animal (typically a mammal such as a dog, cat, horse, cow, sheep or pig) or a human. Preferably, the method is used to treat humans. Typically, the method is used to treat sex hormone-dependent tumours, such as tumours (or cancer) of the breast, prostate, ovary, endometrium or testicles.

It may be particularly advantageous to treat those patients who, following biopsy, are shown to have tumours with a high degree of steroid independency.

Existing therapies deprive tumours of the steroids required for their growth while having perhaps a negligible potency with respect to directly destroying the tumour cell. The compounds for use in the methods of the invention (and identifiable using the screening method) both have a capacity to control pituitary hormone secretion and directly destroy the tumour cell. Neoplasms that grow independently of steroids are resistant largely to existing therapies since their direct anti-tumour efficacy has not been specifically selected for. In addition, conventional agonist based tumour therapeutics induce the unwanted side effect of "flare" of initial excess pituitary hormone release, which we believe will be avoided using the compounds described and identifiable using the screening method herein. Because the compounds act principally on the tumour, pituitary desensitisation does not occur and the compounds are less likely to lead to resistance to the compound.

When hyperplasia is treated, it is particularly preferred to treat benign prostate hyperplasia (BPH) or uterine fibroids (also known as leiomyomas).

The compounds for use in the methods of treatment of the invention will normally be administered by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses. In particular, the compounds for use in the methods of treatment of the invention may be applied directly to the uterine lining.

In human therapy, the compounds for use in the methods of treatment of the invention can be administered alone but will generally be administered in admixture with a suitable pharmaceutical excipient, diluent or carrier selected with regard to the intended route of administration and standard pharmaceutical practice.

The compounds for use in the methods of treatment of the invention can also be administered parenterally, for example, intravenously, intra-arterially, intraperitoneally, intrathecally, intraventricularly, intrasternally, intracranially, intramuscularly or subcutaneously (which is a preferred route of administration), or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For parenteral administration to human patients, the daily dosage level of the compounds of the invention will usually be from 1 to 1000 mg per adult (i.e. from about 0.015 to 15 mg/kg), administered in single or divided doses. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds for use in the methods of treatment of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains at least 1 mg of a compound of the invention for delivery to the patient. It will be appreciated that he overall daily dose with an aerosol will vary from patient to patient, and may be administered in a single dose or, more usually, in divided doses throughout the day.

Alternatively, the compounds for use in the methods of treatment of the invention can be administered in the form of a suppository or pessary, or they may be applied topically in the form of a lotion, solution, cream, ointment or dusting powder. The compounds of the invention may also be transdermally administered, for example, by the use of a skin patch.

For application topically to the skin, the compounds for use in the methods of treatment of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

For veterinary use, a compound for use in the methods of treatment of the invention is administered as a suitably acceptable formulation in accordance with normal veterinary practice and the veterinary surgeon will determine the dosing regimen and route of administration which will be most appropriate for a particular animal.

A further aspect of the invention provides use of a compound selected according to the invention or a compound which (a) binds a GnRH receptor; (b) selectively activates signalling via G$\alpha$i and does not activate signalling via G$\alpha$q; and (c) produces a 2-fold or greater increase in Erk1/2 phosphorylation over basal levels in a benign hyperplastic cell in the manufacture of a medicament for combating tumours or reproductive tissue hyperplasias.

It will be appreciated that the methods of treatment of the invention may comprise the administration to the patient of a further agent, such as an anticancer agent.

Cancer chemotherapeutic agents include: alkylating agents including nitrogen mustards such as mechlorethamine ($HN_2$), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazolecarboxamide); Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycoformycin). Natural Products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; and biological response modifiers such as interferon alphenomes. Miscellaneous agents including platinum co-ordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MIH); and adrenocortical suppressant such as mitotane (o,p'-DDD) and aminoglutethimide; taxol and analogues/derivatives; and hormone agonists/antagonists such as flutamide and tamoxifen. Other agents include paclitaxel, bombesin, gastrin releasing peptide (GRP) antagonists, and iressa (gefitinib; an EGF antagonist).

The invention will now be described in more detail by reference to the following Figures and non-limiting Examples.

FIG. 1 shows the anti-proliferative effects of GnRHR-interacting ligands upon human JEG-3 choriocarcinoma cells. Low cell density JEG-3 cell subcultures were treated for 5 days continuously with the indicated doses of GnRH I (a), GnRH II (b), antagonist 135-18 (c) or antagonist 135-25 (d) added directly to Dulbecco's modified Eagles medium supplemented with 10% FCS, glutamine and penicillin/streptomycin. Ligands were replenished every 24 h. At the end of the stimulation period cells were removed from the growth plates with trypsin and mixed with trypan blue dye (enters non-viable cells). Only viable cells were therefore counted using a haemocytometer in quadruplicate for each ligand dose. The bars in each histogram represent the mean±s.e. mean of n=4 experiments. Both GnRH I and GnRH II demonstrate a potent and dose-dependent anti-proliferative effect upon JEG-3 cells. Antagonist 135-25 (Ant 135-25) displayed a similar potency and efficacy to GnRH I and II whereas antagonist 135-18 (Ant 135-18) demonstrated a much lower potency and efficacy compared to 135-25, GnRH I and II.

Figure 2:
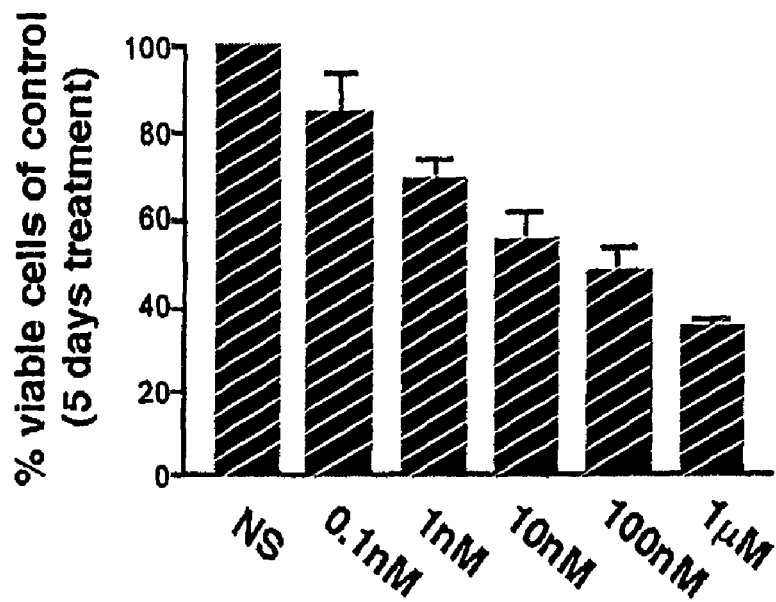
Figure 2:
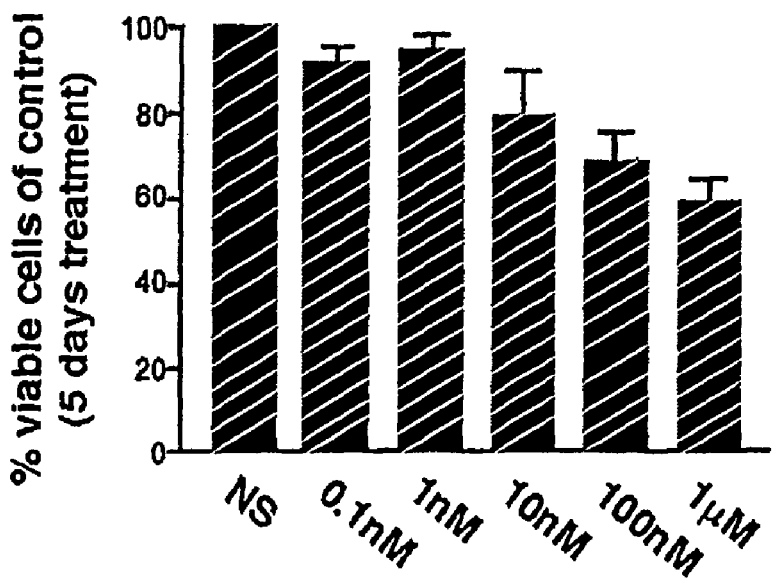
Figure 2:
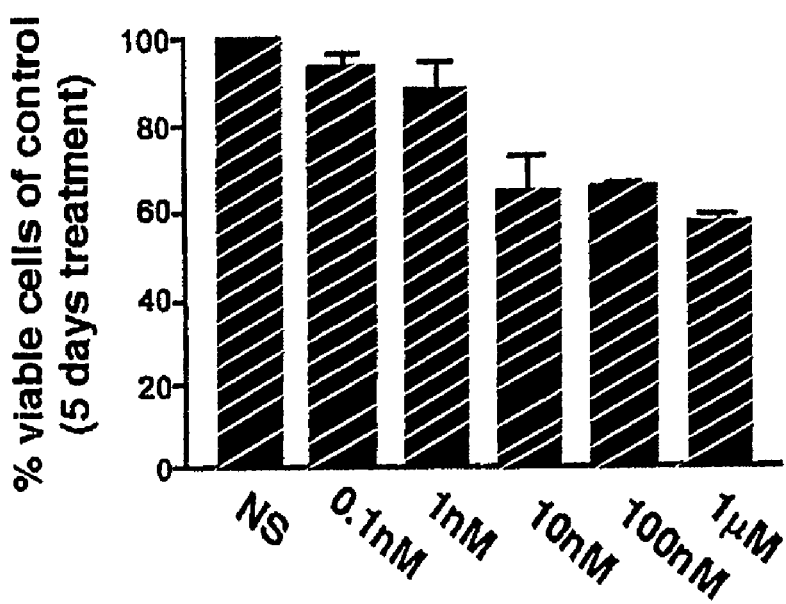
Figure 2:
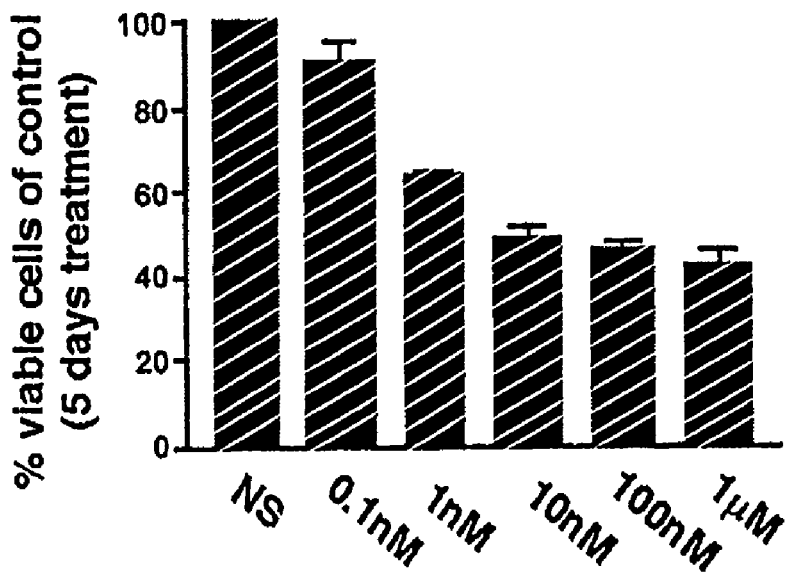

FIG. 2 shows the anti-proliferative effects of GnRHR-interacting ligands upon human benign prostate hyperplastic (BPH-1) cells. Low cell density BPH-1 cell subcultures were treated for 5 days continuously with the indicated doses of GnRH I (a), GnRH II (b), Ant 135-18 (c) or Ant 135-25 (d) added directly to RPMI 1640 medium supplemented with 10% FCS, glutamine and penicillin/streptomycin. Ligands were replenished every 24 h. At the end of the stimulation period cells were removed form the growth plates by trypsin and mixed with trypan blue dye (enters non-viable cells). Only viable cells were therefore counted using a haemocytometer in quadruplicate for each ligand dose. The bars in each histogram represent the mean±s.e. mean of n=4 experiments. Both GnRH I, and to a lesser extent GnRH II, demonstrate a potent and dose-dependent anti-proliferative effect upon JEG-3 cells. Antagonist 135-25 displayed a similar potency and efficacy to GnRH I whereas Ant 135-18 demonstrated a much lower potency and efficacy compared to Ant 135-25 and GnRH I.

Figure 3:
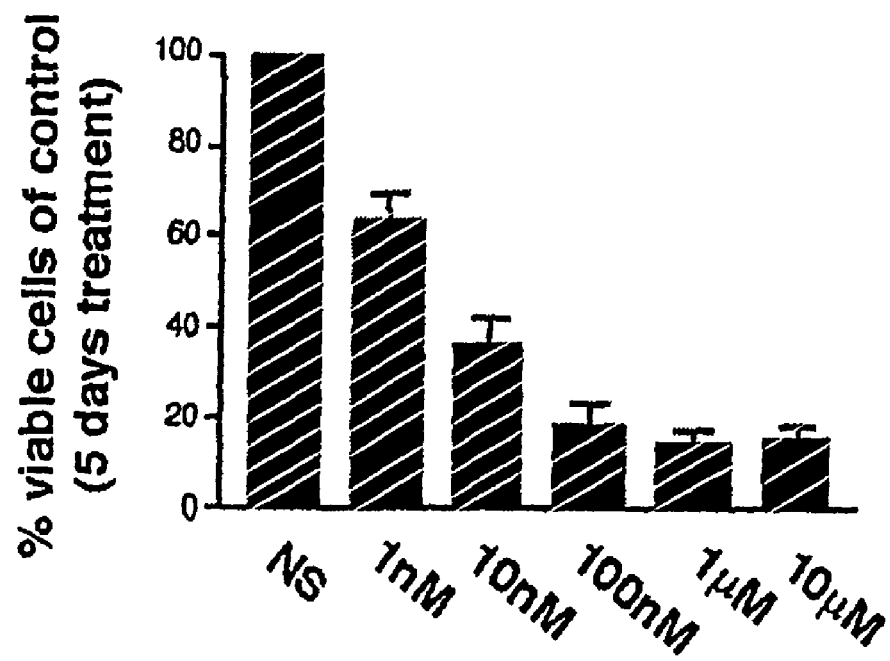
Figure 3:
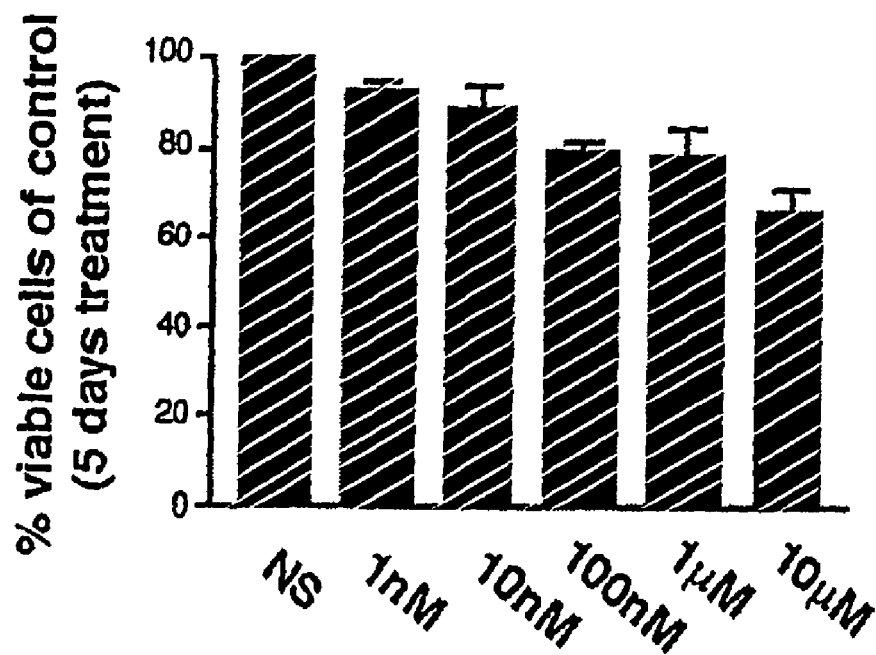
Figure 3:
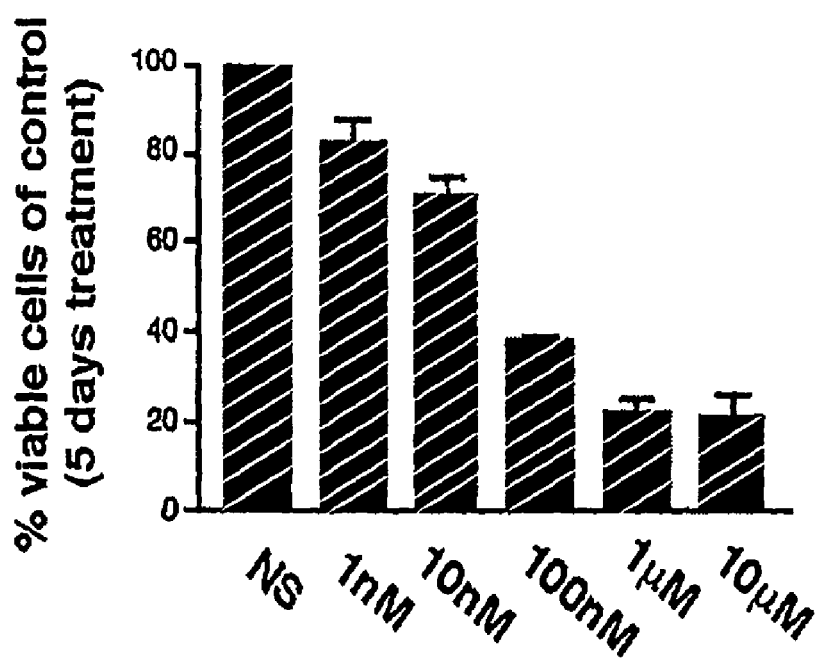
Figure 3:
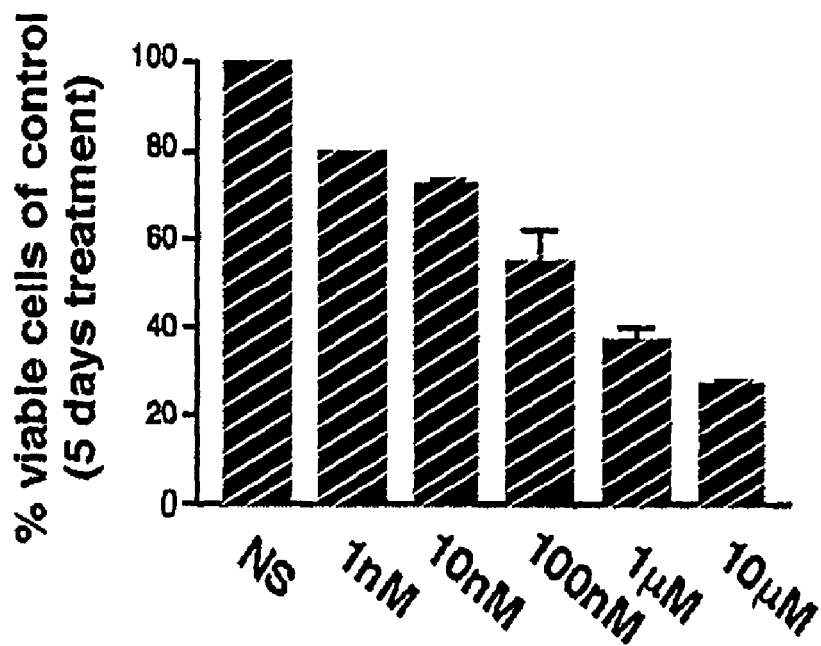

FIG. 3 shows the anti-proliferative effects of GnRHR-interacting ligands upon human embryonic kidney (HEK293) cells expressing the Type I human GnRHR. An identical methodology of measuring cell growth was employed as in FIG. 1. Due to the much greater level of GnRHR expression in the SCL60 cells (HEK293 cells stably overexpressing the human Type I GnRHR) a greater anti-proliferative efficacy is evident for GnRH I (a), II (b) and Ant 135-25 (d). However, Ant 135-18 (c) still displays a low efficacy compared to the other ligands.

Figure 4:
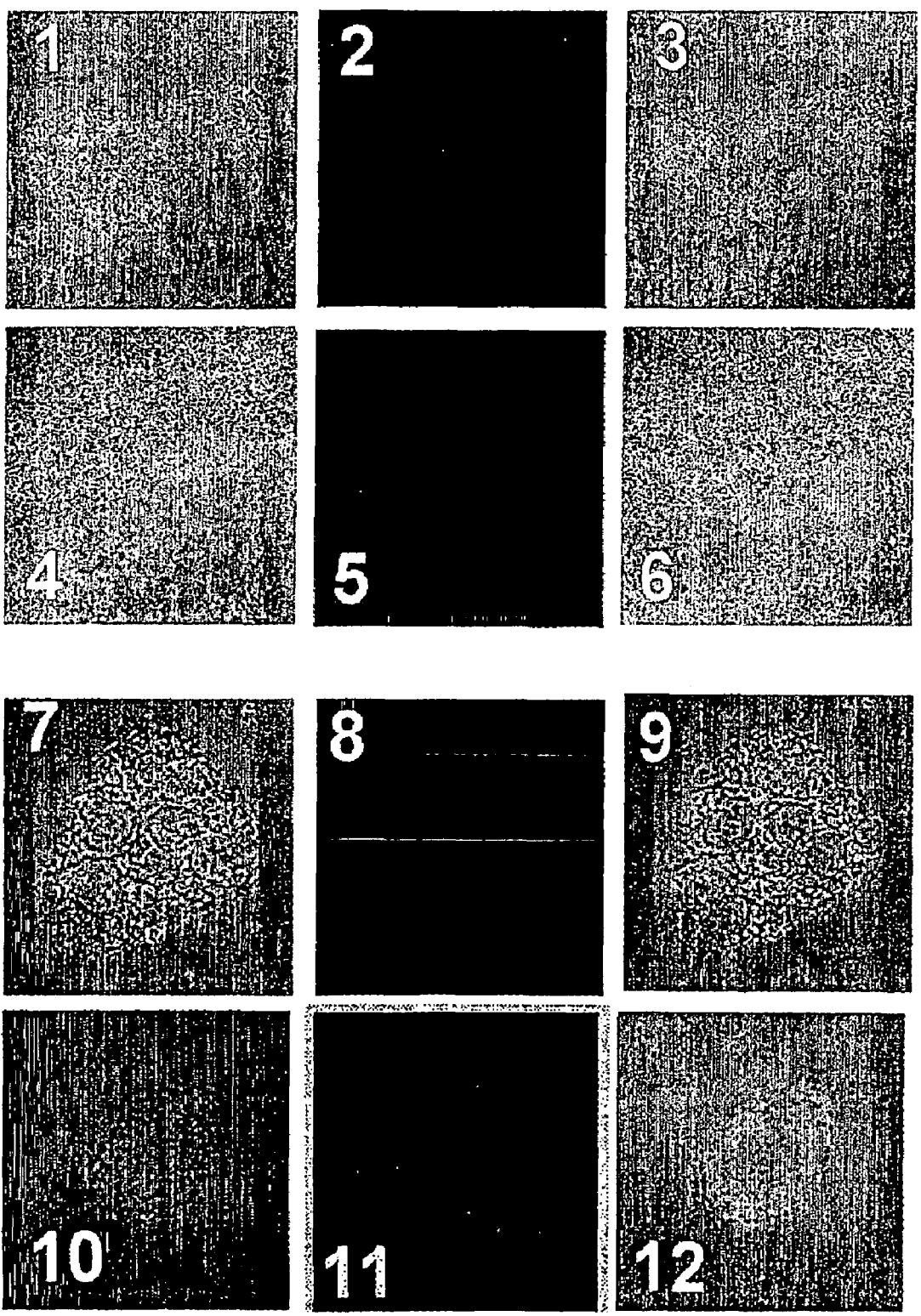
Figure 4:
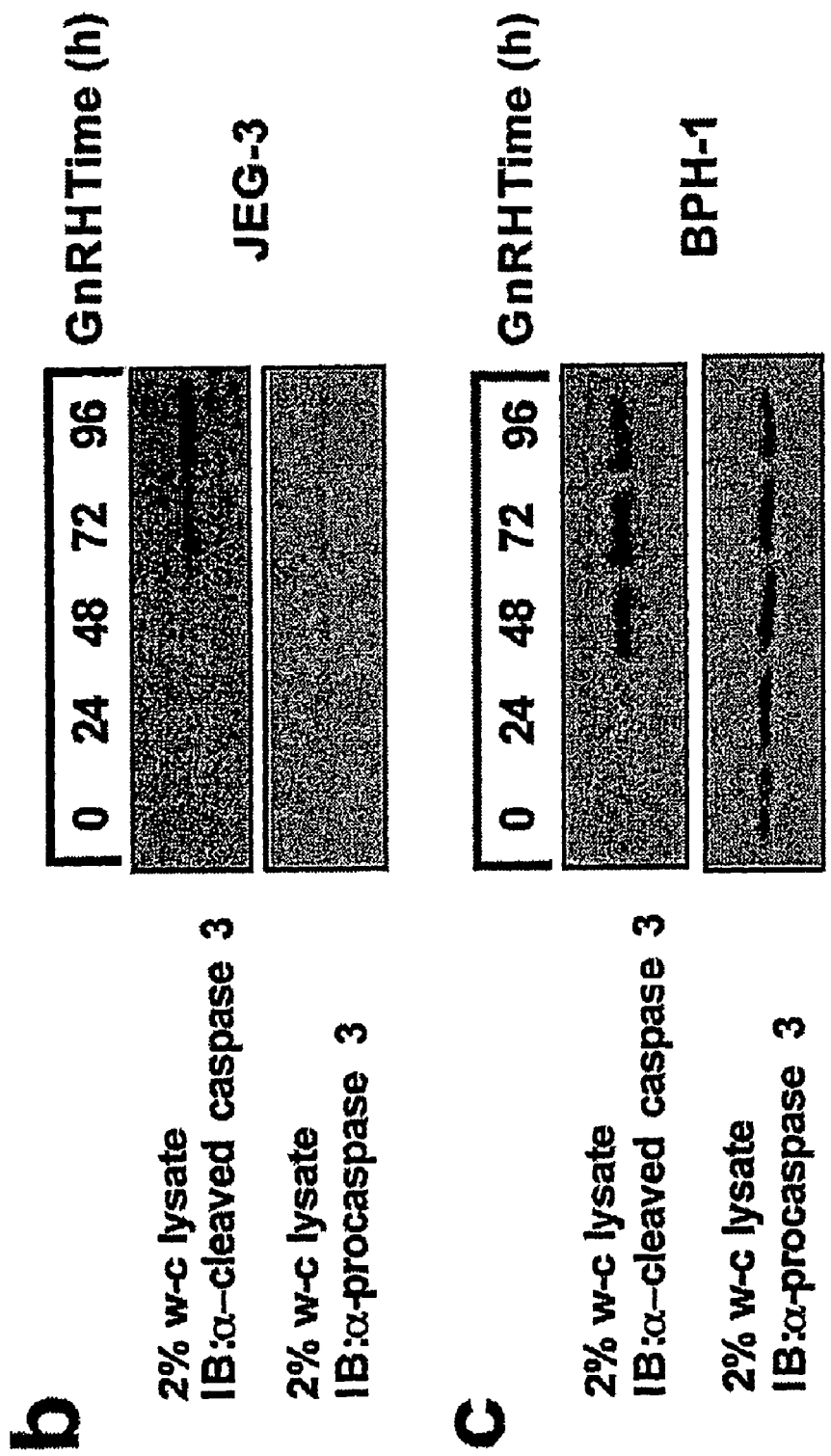

FIG. 4 shows the GnRH-induced apoptotic events in JEG-3 and BPH-1 cells. a) GnRH-induced plasma membrane translocation of phosphatidylserine measured using annexin V-FITC recombinant protein staining. All twelve panels depict either phase contrast (1, 4, 7, 10), confocal laser microscope (2, 5, 8, 11) or phase contrast/confocal merged images (3, 6, 9, 12). Panels 1 to 3 depict untreated control JEG-3 cells for cells in panels 4 to 6 which have been treated with GnRH I (100 nM) for 24 h. All cells have been exposed while live to an annexin V recombinant protein conjugated to the FITC fluorophore. The annexin V will bind specifically only to phosphatidylserine (PS) lipids usually only expressed on the intracellular side of the plasma membrane lipid bilayer. An early sign of apoptosis is the translocation of these PS lipids from the intracellular side of the membrane to the outer aspect of the bilayer. As can be seen in panels 2 or 5 there is no significant expression of annexin-V-reactive PS on the extracellular surface of the plasma membrane. Panels 10 to 12 depict cells exposed to GnRH I for 48 h while panels 7 to 9 serve as unstimulated contemporaneous controls. It is evident in panel 11 that there is significant expression of extracellular annexin-V-reactive PS on the JEG-3 cell membrane. Identical results were gained from similar GnRH I treatment of BPH-1 cells (data shown in further figures). GnRH I induces an enhanced expression of the pro-apoptotic proteases cleaved-caspase 3 and procaspase 3 in both JEG-3 cells (b) and BPH-1 cells (c). The cellular levels of caspase 3 and procaspase 3 were assessed by specific immunoblotting of JEG-3 or BPH-1 whole cell (w-c) lysates from cells stimulated continuously with GnRH I for the times depicted.

Figure 5:
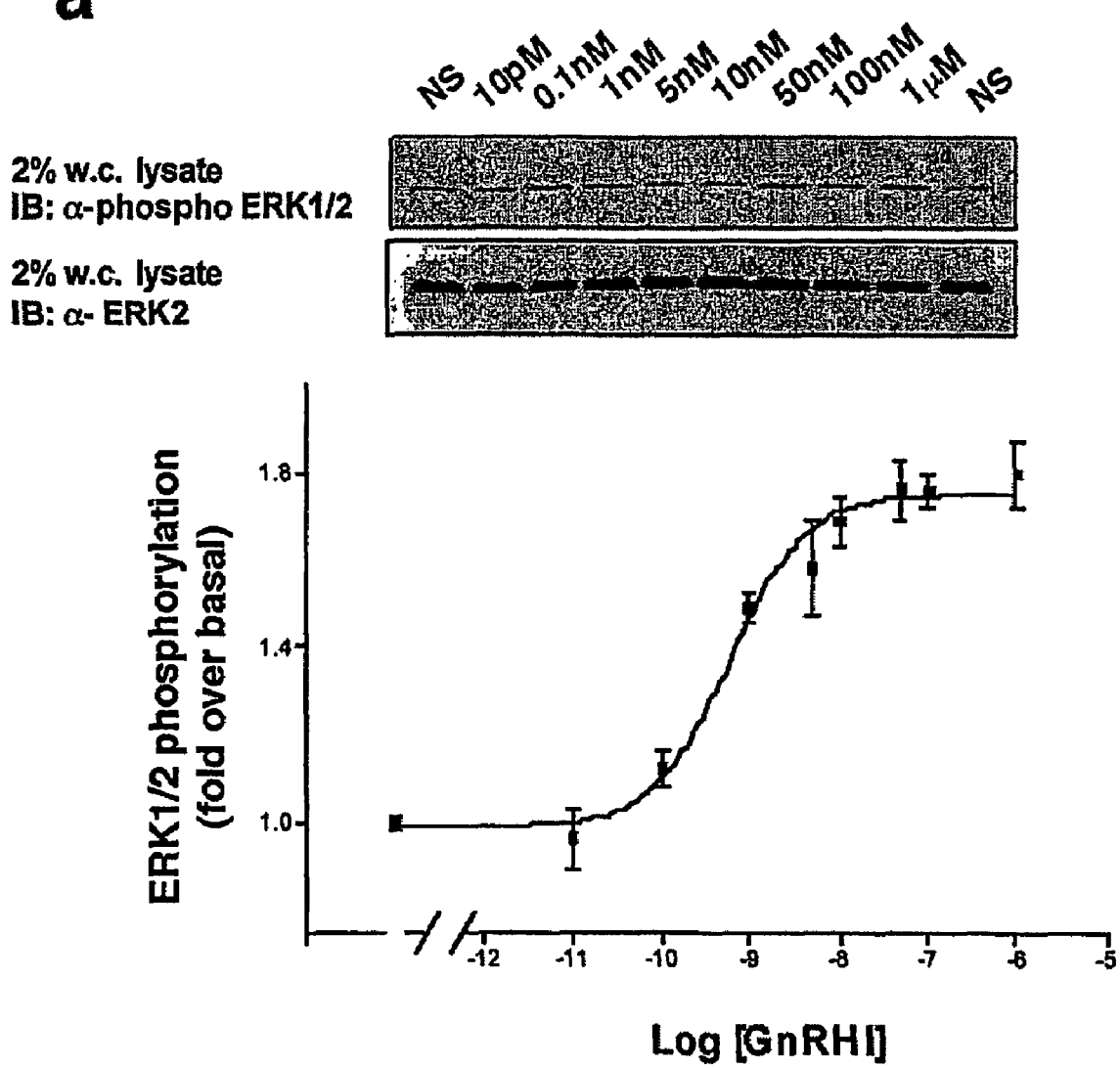
Figure 5:
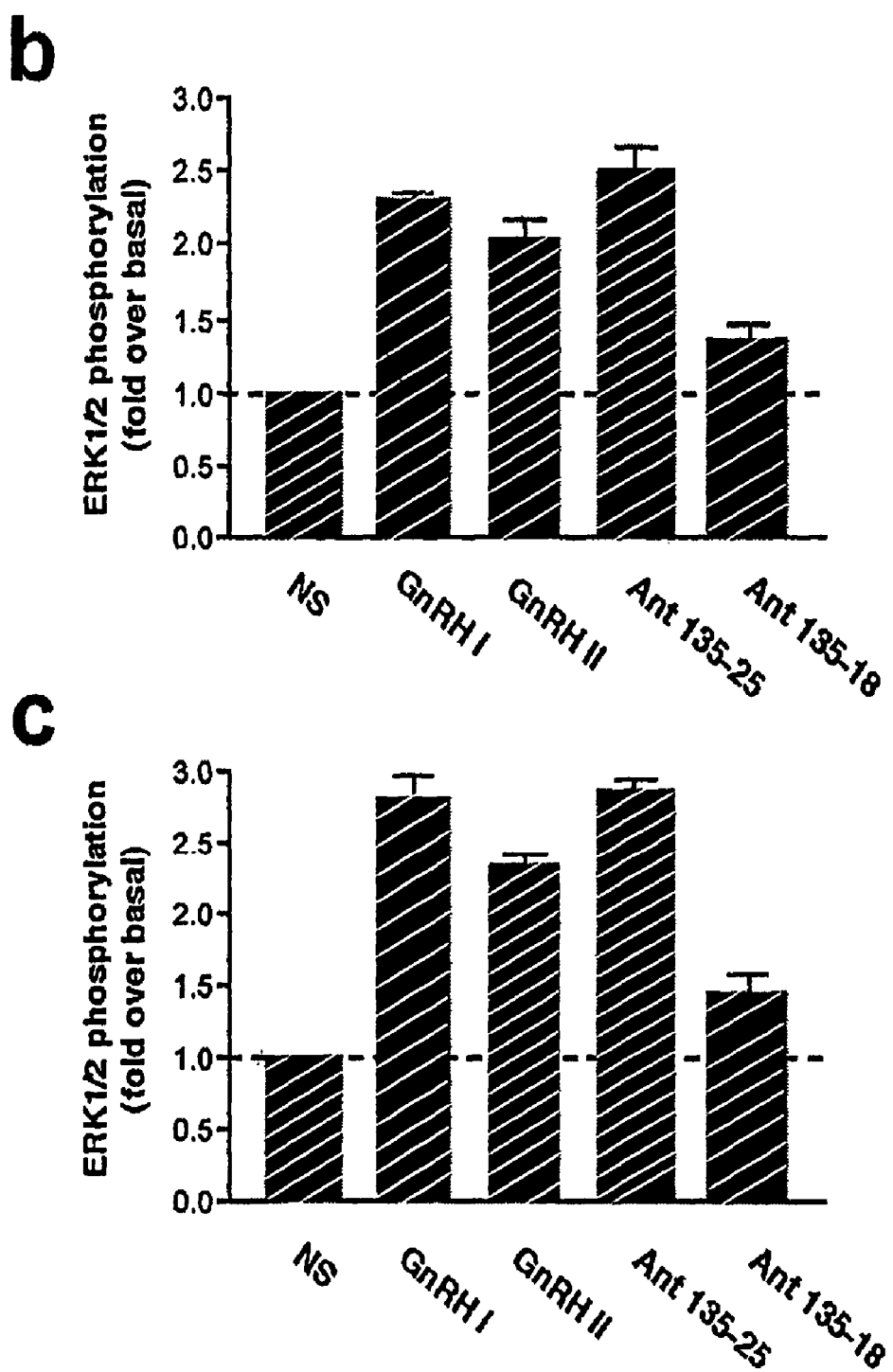

FIG. 5 shows that GnRHR-interacting ligands stimulate extracellular signal regulated kinase (ERK1/2) in both BPH-1 and JEG-3 cells. a) GnRH I induces a strong and dose-dependent activation of ERK1/2 in BPH-1 cells. The panel depicts a representative anti-phospho-ERK1/2 w-c lysate immunoblot of stimulated BPH-1 cell extracts. The phospho-specific antisera identifies the activated form only of ERK1/2 while the anti-ERK2 sera reacts equally inactive and active forms of ERK2. Similar results were achieved when similar studies were performed upon JEG-3 cells, confirming other studies of GnRH-induced JEG-3 cell activation. Panel b) depicts the extent of ERK1/2 phosphorylation and hence activation, in JEG-3 cells induced by several GnRHR-interacting ligands (all at 100 nM dose for 10 minutes). Each bar of the histogram represents the mean±s.e. mean of three to four experimental replicates. Both GnRH I and Ant 135-25 activate ERK1/2 to a similar extent, with GnRH II being less effective with Ant 135-18 the least effective. Panel c) depicts the extent of ERK1/2 activation in BPH-1 cells induced by stimulation with GnRH I, II, Ant 135-25 and Ant 135-18. A similar pattern to JEG-3 of ligand activation of the BPH-1 cells was observed. Each bar of the histogram represents the mean± s.e. mean of three to four experimental replicates.

Figure 6:
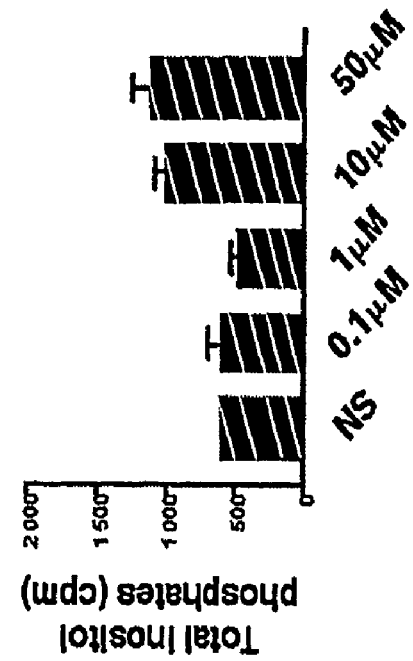
Figure 6:
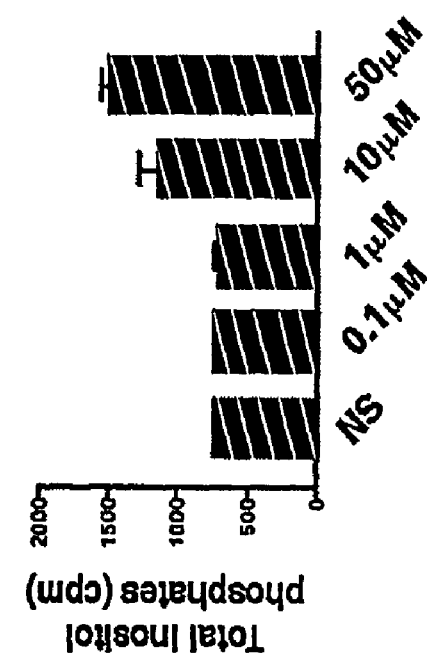
Figure 6:
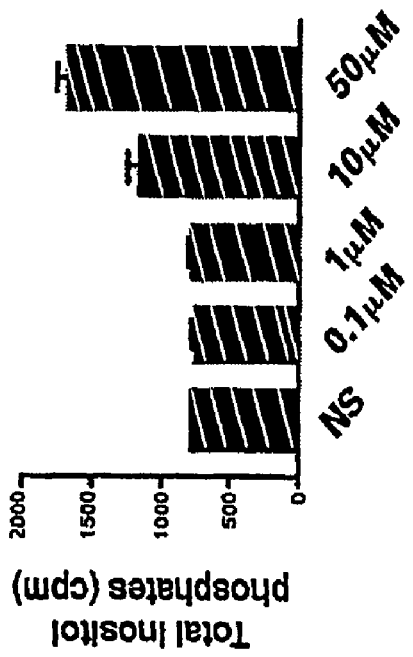
Figure 6:
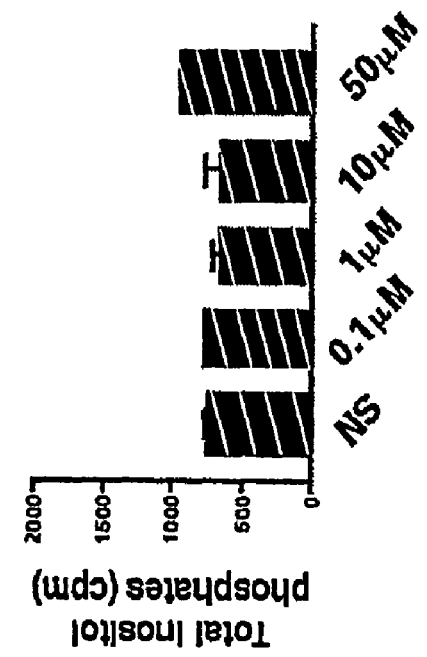
Figure 6:
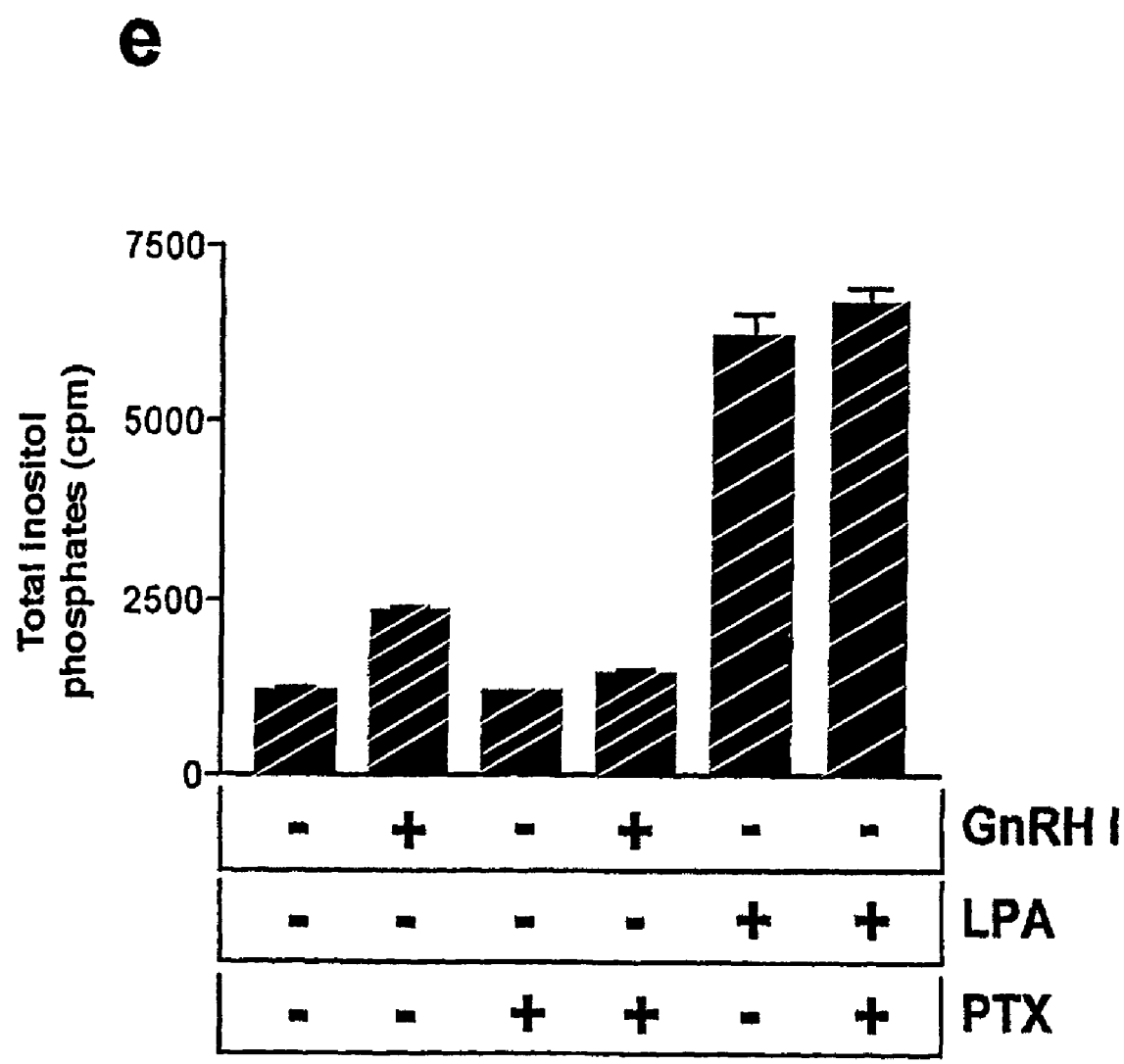

FIG. 6 shows the induction of inositol phosphate accumulation by GnRHR-interacting ligands in BPH-1 cells. BPH-1 cells were pre-incubated with $^3$H-myoinositol (1 μCi/ml) for 48 h prior to ligand stimulation (60 minutes). Ligand stimulated inositol phosphate production was measured in the presence of 10 mM LiCl. Panels a to d demonstrate that only high doses of GnRH I and Ant 135-25 cause any significant accumulation of inositol phosphates, suggesting that expression of the Type I GnRHR is predominant in these cells. This has been confirmed by RT-PCR (data not shown), the poor activity of GnRH II upon inositol phosphate accumulation is probably due to the lower sensitivity of the inositol phosphate assay as compared to the highly amplified ERK1/2 activation assay. The high doses though required of GnRH I to induce significant inositol phosphate accumulation suggested that the primary effector of PLC-β activation, Gαq, may not be the mechanism by which the inositol phosphates accumulation is being induced. IP accumulation can be used as a read out/marker for Gαq activation since the activation of PLCβ is PTX-resistant. Panel e demonstrates that a Gαi mechanism may be responsible for this high dose GnRH I effect. Hence the capacity of the high dose of GnRH I (50 μM) to induce an inositol phosphate accumulation was abrogated by a 16 h pre-incubation of the BPH-1 cells with 200 ng/ml of pertussis toxin (PTX). In contrast the inositol phosphate accumulation induced the potent cell mitogen lysophosohatidic acid (LPA) was insensitive to PTX pre-incubation suggesting that the LPA GPCR in these cells can still stimulate PLC-β activation independently of Gαi.

FIG. 7 shows the GnRH-induced activation of JNK and p38 mitogen-activated protein kinases in JEG-3 and BPH-1 cells. The activation of two other forms of mitogen-activated protein kinase (MAPK) was studied in JEG-3 and BPH-1 cells by overexpressing myc-tagged constructs of JNK2 or p38α. Immunoprecipitation of these constructs after GnRHR-ligand stimulation of either cell line allowed the degree of kinase activation to be assessed using antisera specific for the active, phosphorylated, form of the kinase. In both cell lines there was a potent stimulation of these MAPKs, however there appeared to a be a cell-dependency of the kinase stimulated, thus in JEG-3 cells only a significant activation of the immunoprecipitated myc-JNK2 was demonstrated (Panel a, p38α data not shown) while in BPH-1 cells only a significant activation of myc-p38α was detected (Panel b, JNK2 data not shown). In both panel a and b, the dose of GnRH I employed was 100 nM. The respective histograms in each panel represent the mean±s.e. mean of three experimental replicate time courses.

FIG. 8 shows the ligand-specific activation of JNK or p38 MAPK in JEG-3 and BPH-1 cells. Panel a demonstrates that both GnRH I and Ant 135-25 can efficiently activate the myc-JNK2 construct, measured by its activated phosphorylation status, while a similar cellular stimulation with Ant 135-18 fails to efficiently activate JNK. The inset immunoblots depict the phosphorylation status of the immunoprecipitated JNK2 increasing while the level of total unphosphorylated protein (detected with α-JNK antisera) remains unchanged. The histogram below depicts the mean±s.e. mean of three experimental replicates of the above western blot. Stimulation of BPH-1 cells with the same range of ligands (Panel b) yields a similar pattern of MAPK activation, but in this case p38α. Hence both GnRH I and Ant 135-25 effectively activate p38α while Ant 135-18 does not. The inset immunoblots depict an increasing phosphorylation of p38α with no increase in total p38α protein. The histogram below depicts the mean±s.e. mean of three experimental replicates of the above western blot.

Figure 9:
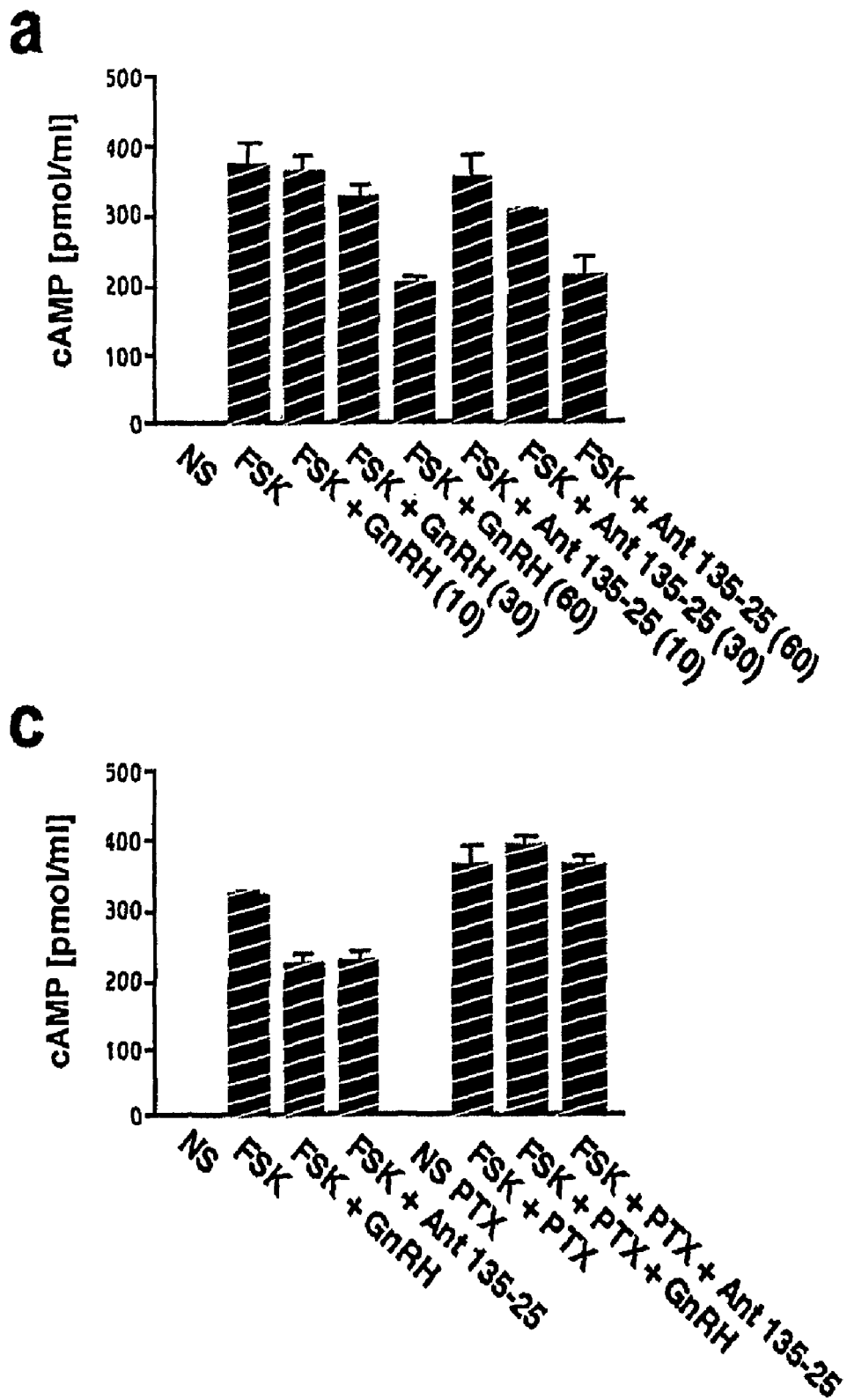
Figure 9:
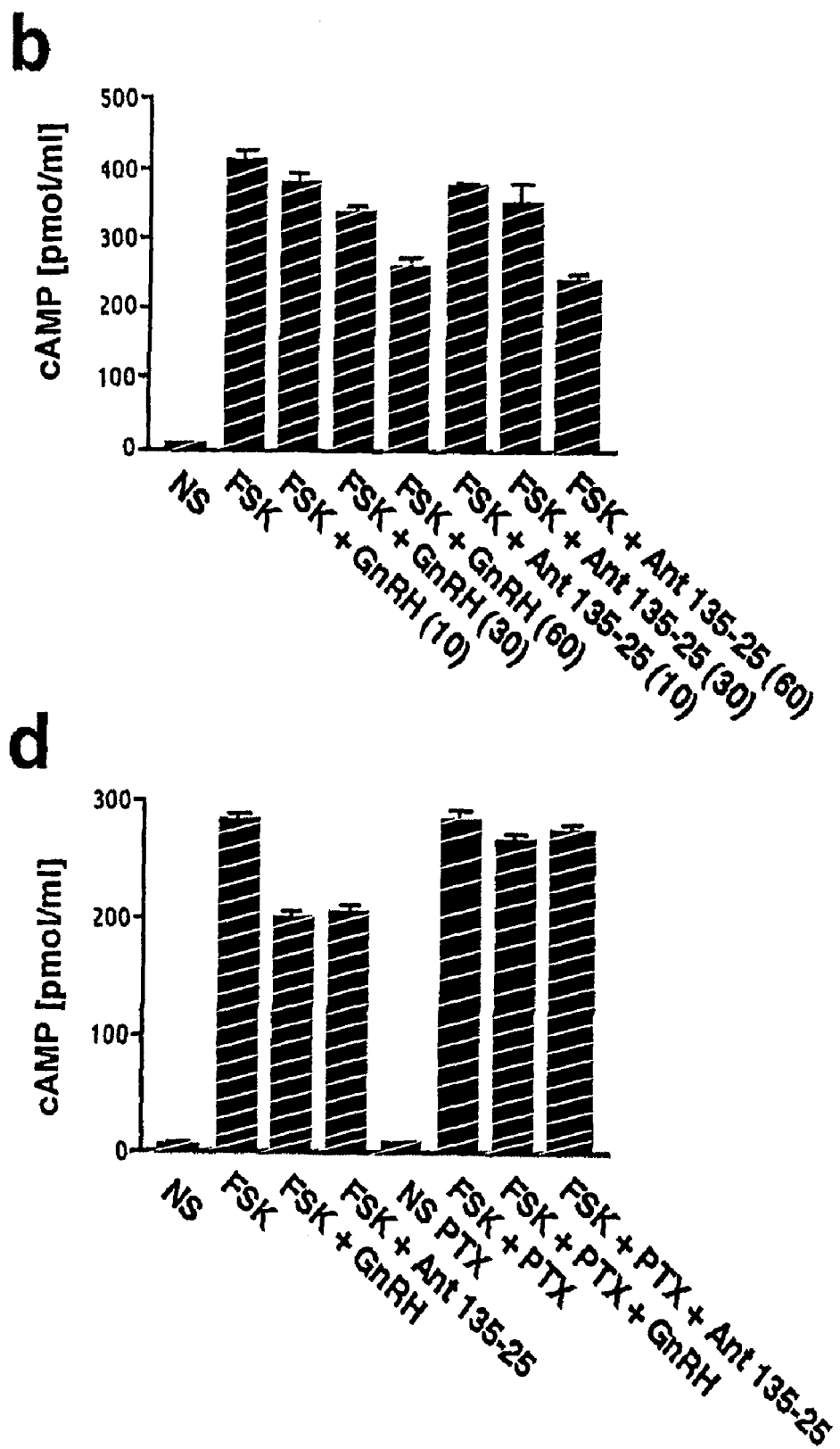

FIG. 9 shows that GnRH I and Ant 135-25 activate the Gαi-type G protein. In both BPH-1 and JEG-3 cells GnRH and Ant 135-25 can antagonize forskolin (FSK) stimulated intracellular cAMP accumulation. Panels a and b respectively depict the effects of FSK, GnRH I and Ant 135-25 upon intracellular levels of cAMP in BPH-1 and JEG-3 cells measured using a calorimetric Biomol cAMP assay kit. As can be seen in panels a and b a single stimulation with FSK (2 μM, 15 minutes) potently elevates intracellular cAMP levels. However with increasing times of pre-exposure (10, 30, 60 minutes) to GnRH I or Ant 135-25 the extent of FSK-stimulated cAMP accumulation was significantly reduced. The most potent inhibition of FSK-stimulated cAMP accumulation was seen with a 60 minute pre-exposure for both GnRH I or Ant 135-25. In panels c (BPH-1) and d (JEG-3) the GnRH I and Ant 135-25 mediated inhibition of FSK-stimulated cAMP accumulation (60 minute pre-exposure in each case) can be specifically inhibited with a 16 h pre-incubation of the cells with 200 ng/ml of PTX. Each histogram in panels a to d depicts the mean±s.e. mean of three to four experimental replicates of the cAMP accumulation assay.

Figure 10:
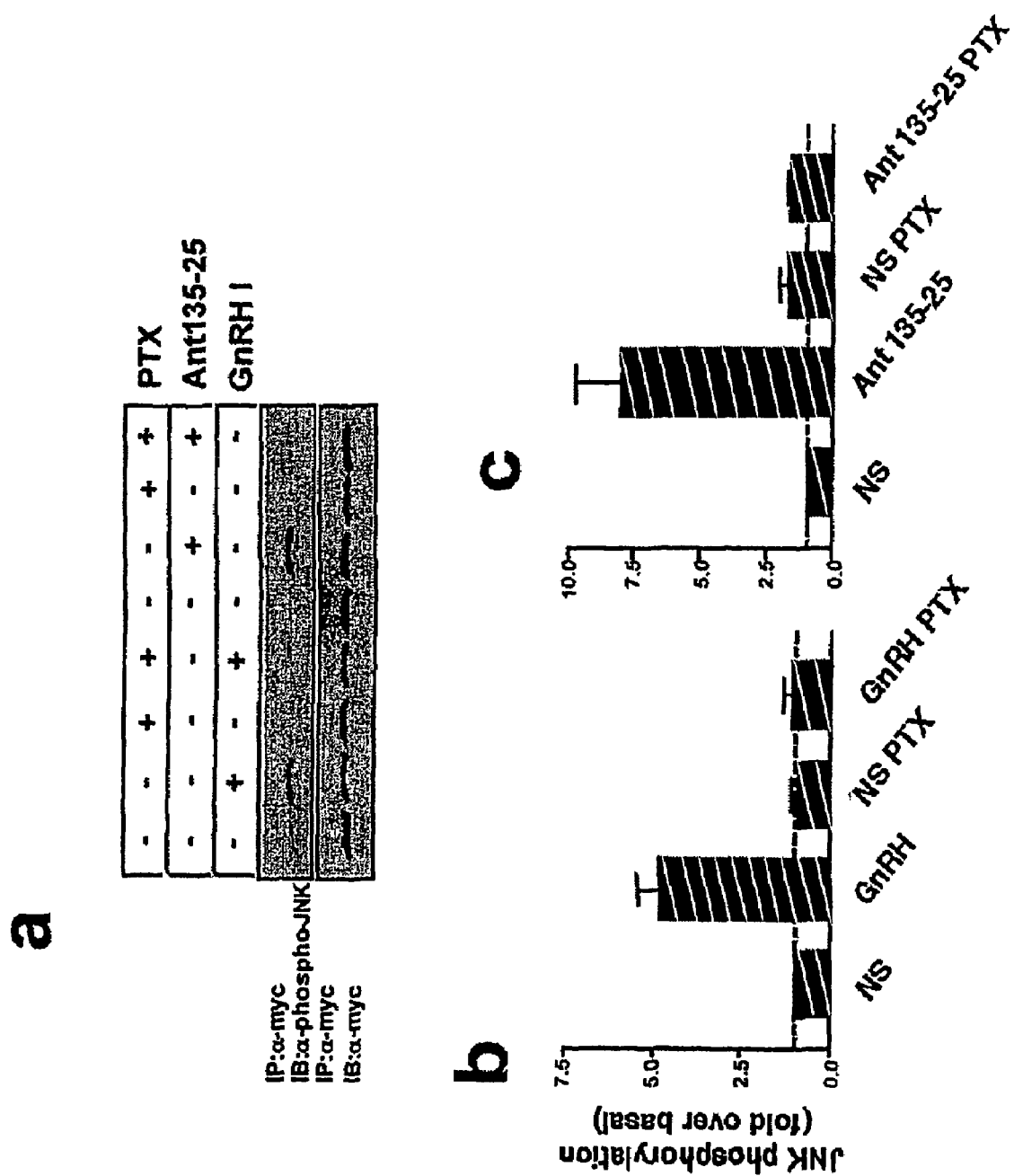
Figure 10:
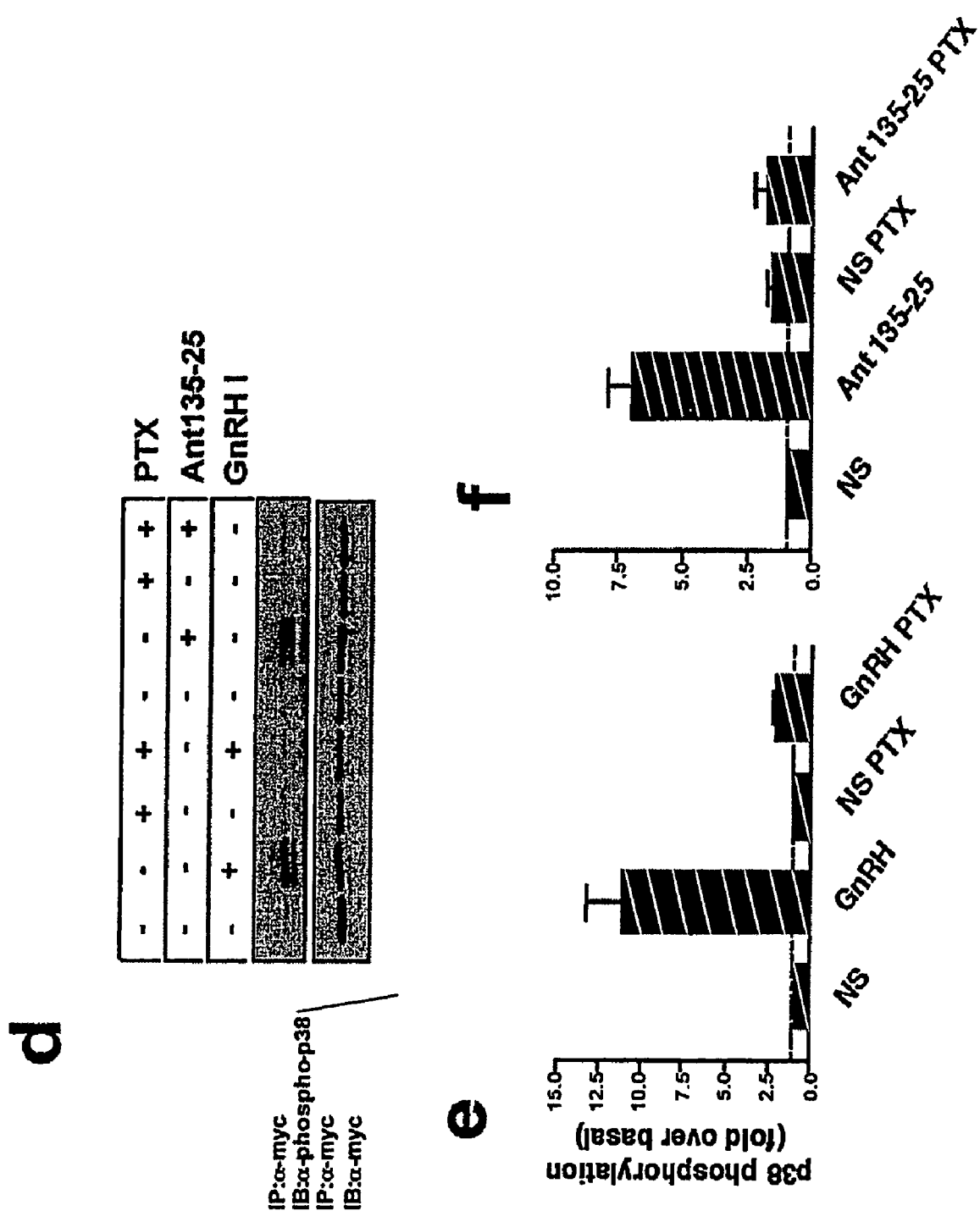

FIG. 10 shows that GnRH I and Ant 135-25 activation of JNK or p38 is dependent upon Gαi stimulation. Stimulation of JNK in JEG-3 cells and p38 in BPH-1 cells and its sensitivity to pre-exposure to PTX was assessed by measuring the degree of activating phosphorylation of immunoprecipitated myc-JNK2 or myc-p38α. Panel a depicts a representative western blot of immunoprecipitated myc-JNK2 from JEG-3 cells stimulated with either GnRH I (100 nM) or Ant 135-25 (100 nM). The phosphorylation status of JNK was elevated by GnRH I and Ant135-25 with no significant alteration in total immunoprecipitated JNK levels (assessed by immunoblot with α-myc antisera). The increases in JNK phosphorylation however was abolished with the PTX pre-incubation (16 h, 200 ng/ml). The histograms in panels b and c depict the mean±s.e. mean of three experimental replicates of the above western blot (panel a) experiments. Panel d depicts an identical experiment to that in panel a except that it is the phosphorylation status of immunoprecipitated myc-p38α that is being measured. Hence as with JEG-3 cells the activation of the MAPK by both GnRH I and Ant 135-25 is acutely sensitive to the pre-exposure of PTX (16 h, 200 ng/ml). The histograms in panels e and f depict the mean±s.e. mean of three experimental replicates of the above western blot (panel d) experiments.

Figure 11:
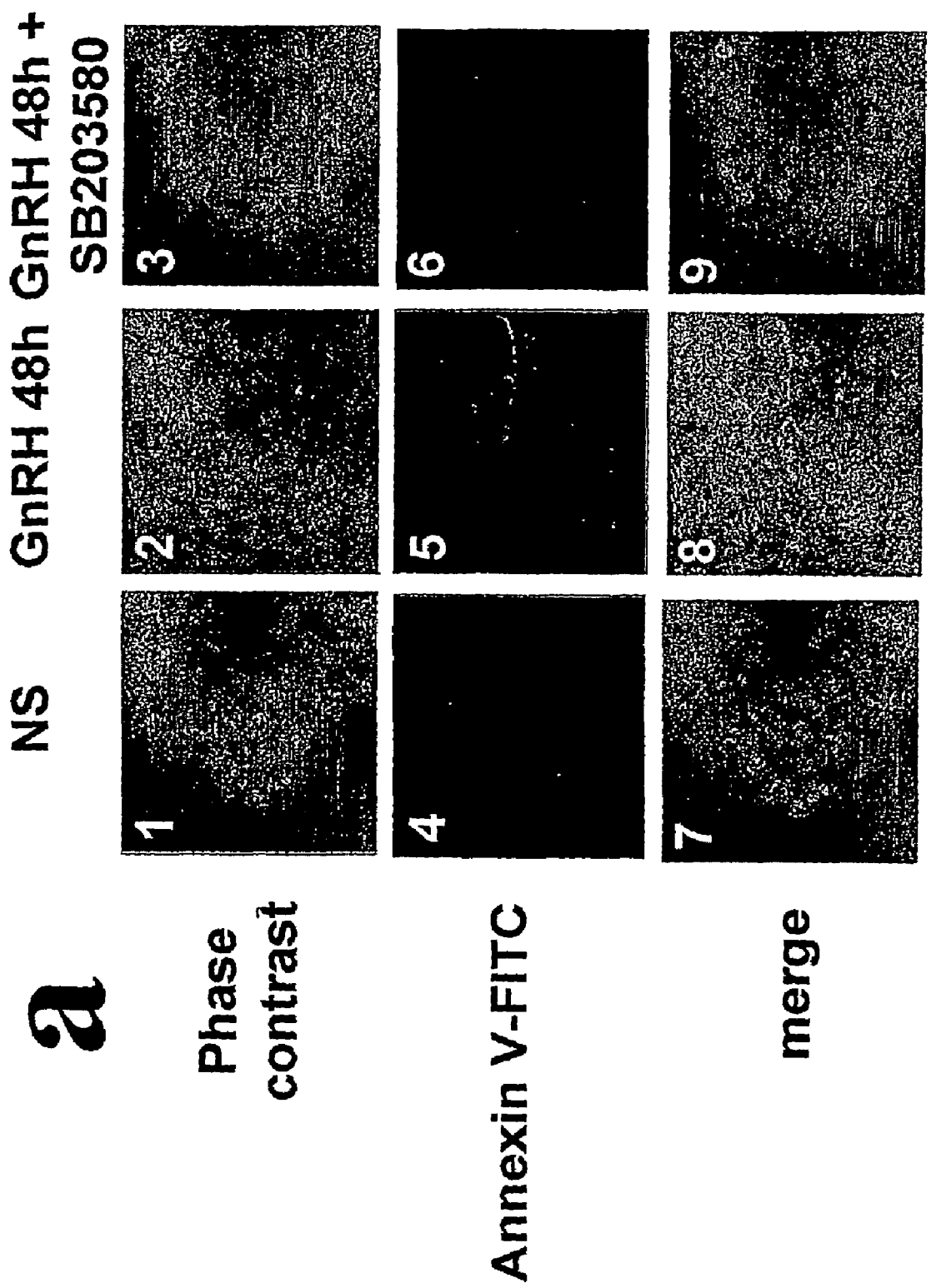
Figure 11:
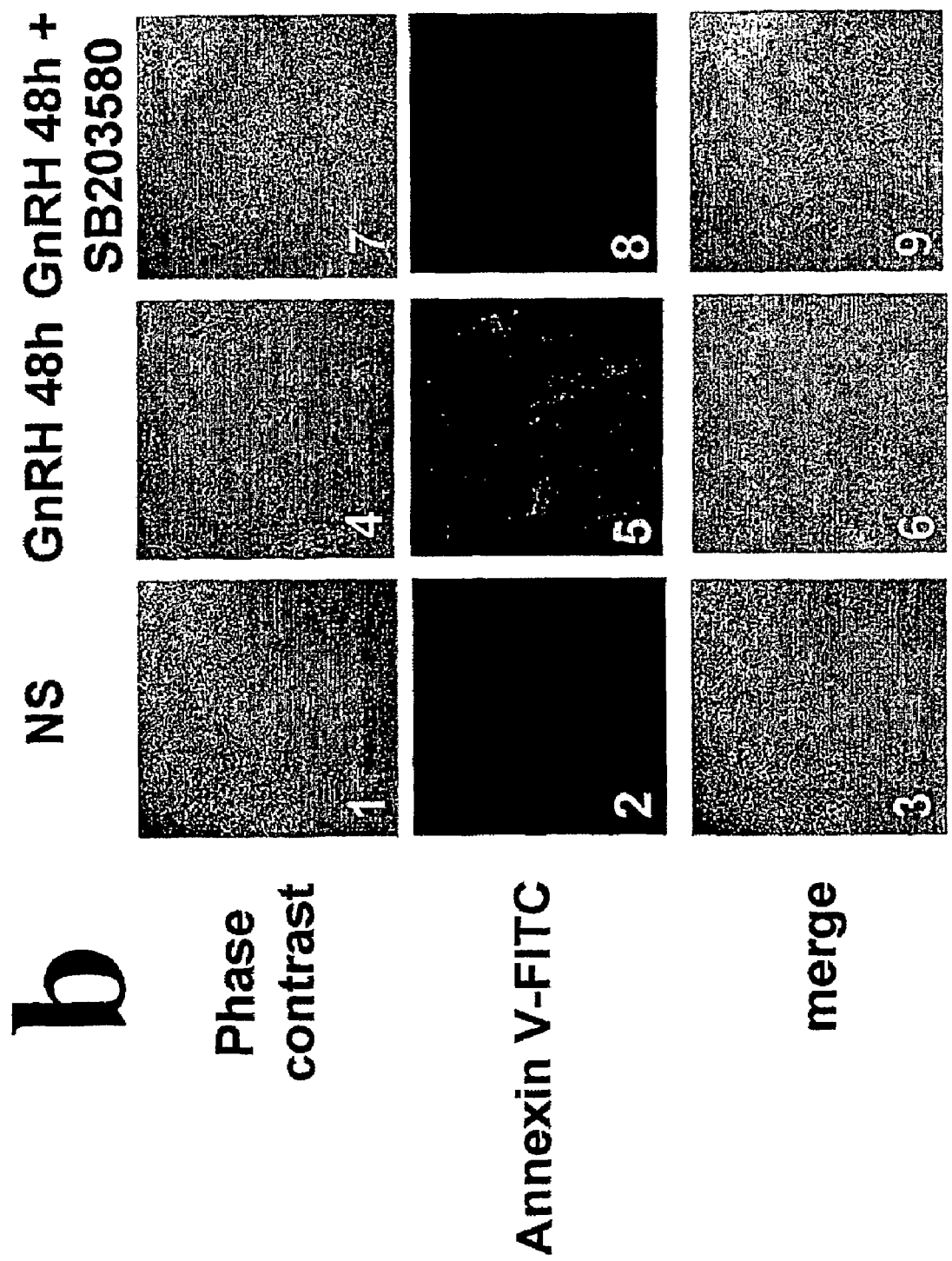

FIG. 11 shows inhibition of GnRH I-mediated apoptosis by selective inhibition of JNK or p38 MAPKs. The contribution of the GnRH-mediated JNK or p38 activation to the pro-apoptotic phenotype of the JEG-3 or BPH-1 cells (demonstrated in FIG. 4) was assessed by using a chemical MAPK inhibitor. Panel a depicts phase confocal microscope images of JEG-3 cells stimulated with 100 nM GnRH I in the presence or absence of a high dose (20 μM of SB203580. This dose of SB203580 effectively abrogates the ability of GnRH I to stimulate JNK in these cells while not significantly affecting the activation of ERK1/2 MAPKs (data not shown). Unstimulated cells (1, 4, 7) demonstrate no annexin V FITC staining indicative of a normal cell membrane morphology, with 48 h of continuous GnRH I treatment cells begin to become anti-annexin V-FITC immunoreactive (2, 5, 8) demonstrating that they have begun to enter an pro-apoptotic state. However when GnRH I is incubated in the presence of SB203580 there is a significant reduction in extent of cells entering a pro-apoptotic state (3, 6, 9). A similar experimental approach was employed for the transfer of this study to BPH-1 cells, however as the MAPK under study in these cells was p38α much lower dose of SB203580 (1 μM) could be employed as the compound has a much greater inhibitory potency against p38 compared to JNK. As with panel a no significant effect of this SB203580 concentration was found upon GnRH-mediated ERK activation in BPH-1 cells, yet this dose significantly blunted the GnRH-mediated activation of p38α (data not shown). As with the effect of SB203580 co-incubation with GnRH in JEG-3 cells inclusion of the chemical inhibitor prevented GnRH from inducing a pro-apoptotic state in the BPH-1 cells (compare 2, 5, 8 with 3, 6, 9).

Figure 12:
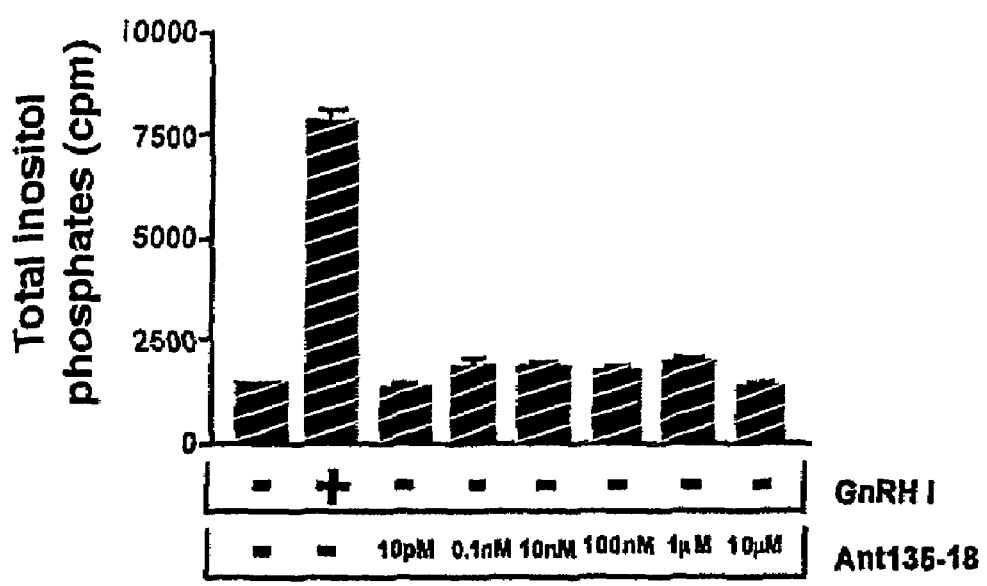
Figure 12:
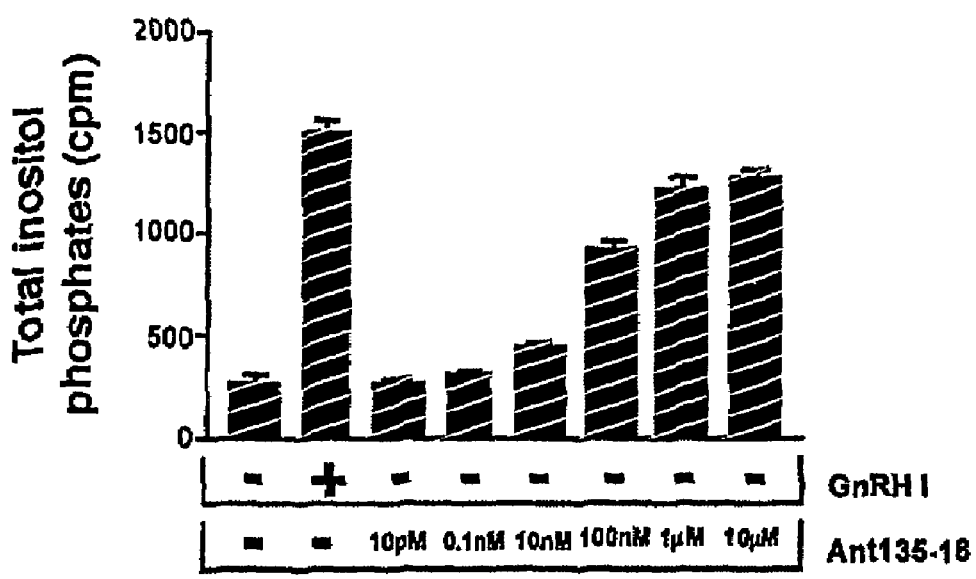
Figure 12:
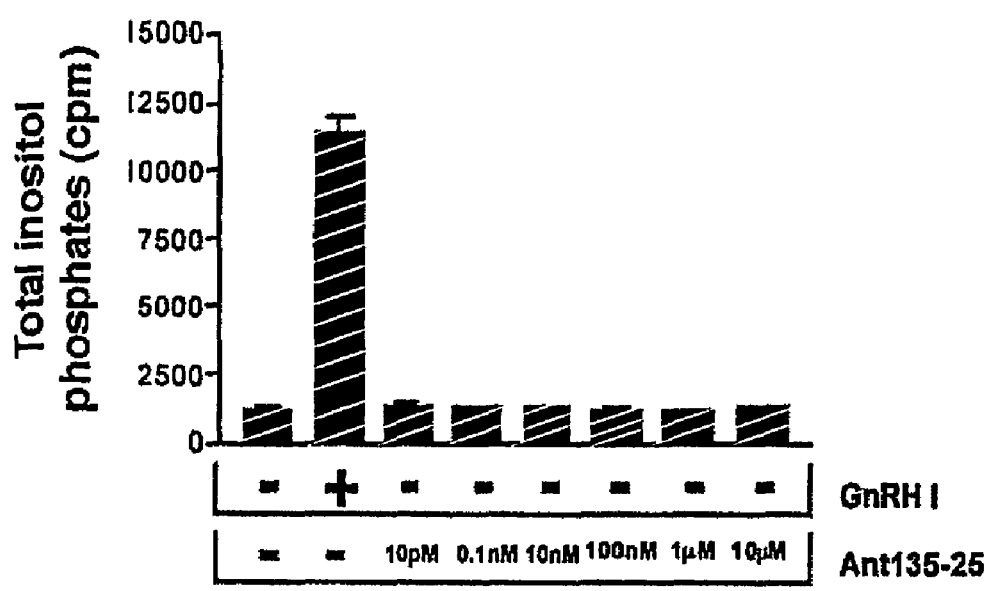
Figure 12:
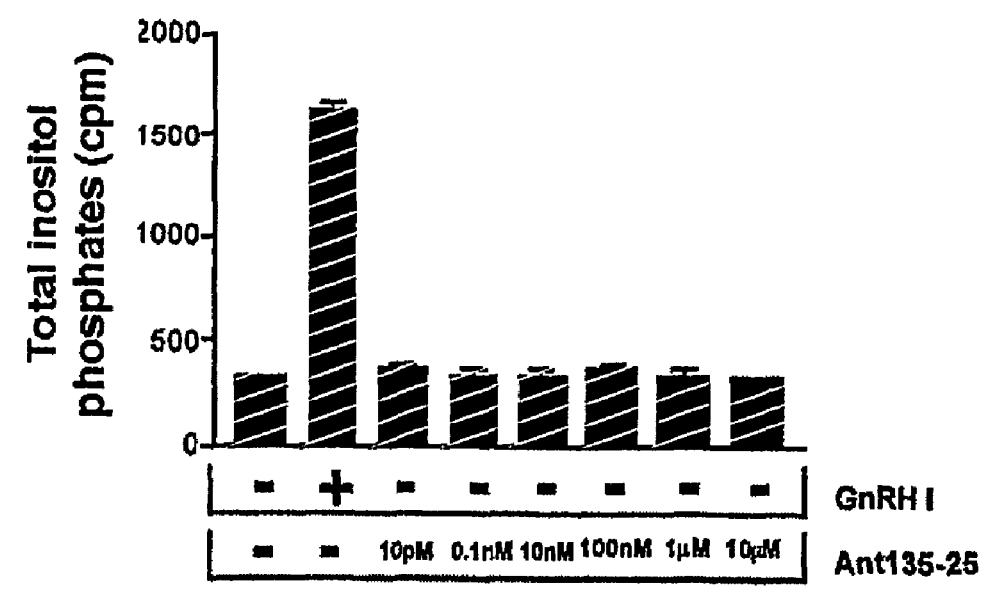

FIG. 12 shows that Ant 135-25 possesses a distinct pharmacological profile to Ant 135-18. Using two cell lines expressing a single GnRH receptor population it can be demonstrated that Ant 135-25 does not seem to exert any significant biological activity at the Type II GnRHR, proposed to be the locus of GnRH action in peripheral tumour cells. The histograms in panels a and b represent inositol phosphate accumulation data from HEK293 cells stably expressing the Type I GnRH receptor only (SCL60). In panel a GnRH I (10 nM) exerts a typical agonistic activity at its cognate receptor demonstrated by the significant increase in liberated inositol phosphates, however at the Type I GnRH receptor even high doses of Ant 135-18 appears to have little classical agonistic capacity. In panel b SCL60 cells are stimulated instead with Ant 135-25 alongside GnRH I, yet again no classical agonistic activity is demonstrated. In panels c and d, the liberated inositol phosphates generated were measured in the proto-gonadotrope cells (αT4) stably expressing the marmoset Type II GnRH receptor (designated αT4-II). In panel c stimulation of the cells with GnRH II (10 nM) results in a similar action to GnRH I upon the SCL60 cells, however Ant 135-18 clearly exerts a dose-dependent agonistic activity upon these Type II GnRH receptor expressing cells. In contrast, panel d, even high doses of Ant 135-25 do not cause any liberation of free inositol phosphates. In both cell lines, SCL60 and αT4-II the free inositol phosphates measured here were liberated in a largely PTX-insensitive manner, suggesting that to some extent Ant 135-25 may primarily exert only an agonistic effect in cellular environments where the GnRH receptor (Type I) is predominantly coupled to Gαi-type G proteins.

EXAMPLE 1

Development of GnRH-Based Anti-Tumour Therapeutic Agents

Four GnRH receptor ligands (GnRH I, GnRH II, and two synthetic GnRH antagonists 135-18 and 135-25) have been screened.

Antagonist 135-18 has the formula: Ac-D-Nal(2)-D-4-ClPhe-D-Pal-Ser-Ile-D-IsopropylLys-Leu-IsopropylLys-Pro-D -AlaNH$_2$.

Antagonist 135-25 has the formula: Ac-D-Nal(2)-D-4-ClPhe-D-Pal-Ser-1-MePal-D-IsopropylLys-Leu-IsopropylLys-Pro-D-AlaNH$_2$.

Abbreviations used:
Ac-D-Nal(2) is acetyl-D-2-naphthylalanine;
D-4-ClPhe is D-4-chlorophenylalanine;
D-Pal is D-pyridylalanine;
Ser is serine;
MePal is methylpyridylalanine;
Ile is isoleucine;
D-IsopropylLys is D-isopropyllysine;
Leu is leucine;
Pro is proline;
Ala is alanine.

Material and Methods

These are described in the legends to the Figures.

Results

GnRH and Ligand Analogues Mediates an Anti-Proliferative Effect Upon Cancerous Tissues Continuous treatment of monolayers of either JEG-3 human choriocarcinoma, human benign prostatic hyperplasia (BPH-1) or HEK293 cells stably expressing the rat type I GnRH receptor (SCL60) resulted in a retardation of the cellular reproductive growth of all three of these cell types. Each cell type was plated at an initial minimal confluency (10-20%) to allow for 5 days of normal continual cell growth that would not result in 100% cell confluency by day 5. Each ligand was incubated, in triplicate for every experimental concentration, with the cell monolayers for five days with replacement of the ligand every 12 h. At the end of the stimulation period the number of viable cells was estimated by their capacity to prevent uptake of Trypan Blue stain. In FIG. 1 it can observed that there are clear dose-response relationships for the inhibition of cellular growth of the JEG-3 cells by GnRH I (panel a), GnRH II (panel b) and the antagonist 135-25 (Ant135-25: panel d). However the antagonist 135-18 (Ant135-18), chemically similar to Ant135-25, failed to demonstrate an anti-proliferative effect of a similar magnitude to that generated by GnRH I, GnRH II or Ant135-25. Thus these data suggest that unlike recent reports (Grundker et al (2002) *J. Clin. Endocrinol. Metab.* 87, 1427-1430) it appears pharmacologically that GnRH I and GnRH II exert a similar effect upon cell proliferation. In addition it appears unlikely that the anti-proliferative GnRH-based effect occurs via a Type II GnRH receptor (GnRHR) stimulation as Ant135-18 has been demonstrated to possess a high degree of partial agonistic activity upon Type II GnRHRs cloned from several species (Ott et al (2002) *Mol. Endocrinol.* 16, 1079-1088) and yet it fails to exert an anti-proliferative action greater than that by Ant135-25 which fails to show any agonistic activity at the Type II marmoset GnRHR.

GnRH and Ligand Analogues Mediates an Anti-Proliferative Effect Upon Hyperplastic Tissues Employing an identical growth and stimulation methodology to that described in the previous paragraph and in FIG. 1 we exposed the hyperplastic cell line, BPH-1, to the same panel of GnRH ligands and antagonistic analogues (FIG. 2). Reminiscent of FIG. 1 both endogenous GnRH agonists exert a similar mode of action with respect to their dose-dependent inhibition of BPH-1 cell growth over the five day stimulation period. However in slight contrast to the JEG-3 cells GnRH I appears to be more potent that GnRH II in its capacity to arrest cell growth. This result directly contrasts recent assertions that indeed a Type II GnRH receptor or a specific GnRH II ligand effect plays a significant role in the anti-proliferative effect of GnRH ligands upon tumour cells. As with the ligand effects upon JEG-3 cells Ant135-25 exerts an anti-proliferative effect upon BPH-1 cells with a similar potency to that of GnRH I while Ant135-18 once again demonstrates a low ant-proliferative potency thus reinforcing the concept that the anti-proliferative effect occurring in these cells is not through a direct action upon a functional human Type II GnRH receptor.

GnRH and Ligand Analogues Mediates an Anti-Proliferative Effect Upon Non-Cancerous Non-Hyperplastic Tissue We further investigated the nature of the ligand-receptor specificity of the anti-proliferative effects of GnRH receptor systems by studying our ligand panel effects upon a model cell background, i.e. SCL60 HEK293 cells stably expressing the rat Type I GnRHR. Upon continuous treatment of the SCL60 cells with GnRH I (FIG. 3, panel a) there was a dramatic reduction in the cells growth rate and significant loss of total cell number. As with the BPH-1 cells the GnRH II ligand appeared less potent than GnRH I at arresting the SCL60 cell growth. The two classical GnRHR antagonist behaved in a similar manner as in the previous two cell lines in that Ant135-18 proved to be relatively ineffective at inhibiting the SCL60 cell proliferation while Ant135-25 had nearly an as efficacious action as either GnRH I or GnRH II. Compared to either JEG-3 or BPH-1 cells there was considerably greater inhibition of cell growth and a greater degree of detectable cell death apparent from 48 h onwards. We attribute this greater effect of the GnRHR ligands upon the SCL60 cells to the much greater level of receptor expression in the SCL60 cells. Only minimal levels of cell surface receptor expression was noted in JEG-3 cells and BPH-1 cells (not in excess of 200 specific cpm for I$^{125}$-His$^5$-Tyr$^6$-GnRH I) while up to a 10-fold greater expression level is demonstrated in SCL60 cells.

GnRH Induces the Generation of Pro-Apoptotic States in Cancerous and Hyperplastic Cells Thus we have shown that upon continuous GnRH ligand stimulation of either JEG-3 or BPH-1 there is a retardation of cell growth, however we were interested as to whether there was any genuine induction of cellular apoptosis recently reported to occur in several tumour cell lines (Soon et al (2002) *J. Clin. Endocrinol. Metab.* 87, 4580-4586). To this end we investigated whether GnRH ligand stimulation of either cell line resulted in the generation of classic signals of apoptosis. Initially we measured the effects of GnRH stimulation upon the ultrastructural integrity of the cells plasma membrane. A well documented early event in apoptosis is a reversal in the polarity of many plasma membrane molecules such as phosphatidylserine (PS). At an early stage of cellular apoptosis there is a significant translocation of PS from the inner to the outer envelope of the plasma membrane. Employing the high affinity of annexin-V protein for exposed PS we tested as to whether protracted GnRH exposure of JEG-3 cells resulted in the expression of annexin-V-reactive PS on the outer envelope of cells stimulated with GnRH I. Unstimulated JEG-3 cells after 24 h of sub-culture failed to demonstrate any extracellular membrane PS as upon incubation for 1 h with annexin-V preconjugated to the FITC fluorophore (1:100 dilution) there was no significant green fluorescence associated with the cells (FIG. 4, panel a, images 1-3). Stimulation of cells for 24 h and then incubation of them with the annexin-V-FITC demonstrated that additionally there was no significant expression of extracellular membrane PS (FIG. 4, panel a, images 4-6). However with a greater period of continuous stimulation (48 h) there was evident a considerable amount of external membrane annexin-V-reactive PS (FIG. 154, panel a, images 10-12). Contemporaneously cultures unstimulated cells in contrast failed to exhibit any external membrane annexin-V-FITC staining (FIG. 4, panel a, images 7-9). Thus after only 48 h of continuous GnRH I stimulation (100 nM) there was induction of plasma membrane reversal as indicated by the presence of extracellular envelope PS. Similar results were obtained from BPH-1 cells for a similar period of GnRH I stimulation (data not shown). In addition to the generation of early plasma membrane PS reversal we also were able to demonstrate additional pro-apoptotic events induced in the cells by protracted GnRH I exposure. Hence we studied the generation of pro-apoptotic caspase enzymes involved in cell degradation in many tissues. Crude whole-cell lysate extracts were made from JEG-3 or BPH-1 cells and the cellular levels of either pro-caspase 3 or its cleaved and active bi-product, caspase-3 were measure by specific immunoblots. In JEG-3 cells stimulated with 100 nM GnRH I continuously there was a significant elevation in the cellular levels of pro-caspase 3 evident from 24-48 h after initial ligand stimulation (FIG. 4, panel b). The generation and elevation of cellular levels of active caspase-3 took longer to emerge and were only significantly evident between 48-72 h of GnRH I incubation. A similar pattern to that in JEG-3 cells of the time-dependent increases in pro-caspase and cleaved caspase-3 in BPH-1 cells during GnRH I stimulation was seen in the BPH-1 cells (FIG. 4, panel c), yet there appeared to be a more rapid onset on the generation of cleaved caspase-3 and a greater basal level of pro-caspase-3 at the initiation of GnRH continuous stimulation.

GnRH Receptor Activation Activates Stress-Activated Protein Kinase Pathways in Hyperplastic and Cancerous Tissue It has been demonstrated by many research groups (Kang et al (2000) *Mol. Cell. Endocrinol.* 170, 143-151; Kimura et al (1999) *Cancer Res.* 59, 5133-5142) that upon stimulation of tumour cell lines there is a potent and protracted stimulation of the extracellular signal-regulated kinase (ERK) isoforms of the mitogen-activated protein kinase (MAPK) family. Coincident with this activation of ERK however is the demonstration of the anti-proliferative action of the GnRH analogues despite the well documented generally proliferative effects of ERK activation in many tissues (Gutkind (1998) *J. Biol. Chem.* 273, 1839-1842). Thus a paradox exists in that the GnRH analogues appear to arrest cell growth and proliferation but potently activate ERK isoforms. Recent data has also demonstrated that an inhibitory effect upon epidermal growth factor receptor (EGFR) activity (Grundker et al, (2001) *Endocrinology* 142, 2369-2380) is in part responsible for the anti-proliferative action of GnRH analogues. However there is significant evidence for the generation of a long lasting ERK activation in peripheral GnRH-responsive tumour tissues and indeed in our experimental paradigms we did indeed observe a reproducible GnRH I-induced activation of ERK1/2 kinases in both JEG-3 and BPH-1 cells (FIG. 5). Compared to the stimulation of other endogenous G protein coupled receptors, e.g. the LPA-responsive EDG-type receptors the degree of ERK1/2 activation was relatively small (data not shown). As with the effects upon cell proliferation we noted that compared to GnRH I, GnRH II and Ant135-25 the potency of Ant135-18 to stimulate ERK1/2 activation was considerably less (FIG. 5, panels b and c). In addition to the activation of ERK1/2 MAP kinases in peripheral tumor cells many reports have demonstrated a lack of inositol phosphate turnover induced by GnRH stimulation. Indeed we also noticed that with low doses of GnRH and its analogues (up 1 to 1 µM) there was no appreciable inositol phosphate turnover (FIG. 6, panels a to d). However at high doses (up to 50 µM) GnRH I, GnRH II and Ant 135-25 all displayed a small capacity to induce inositol phosphate accumulation. The doses that activated this turnover would suggest that rather than PLC-β activation by its cognate G protein (Gαq) that activation of inositol turnover was being mediated by Gβγ subunits of another G protein, e.g. Gαi. Therefore in FIG. 6 panel e, we demonstrated that the GnRH-induced minimal inositol phosphate turnover was sensitive to pretreatment with pertussis toxin (PTX) while the more robust inositol phosphate turnover induced by LPA treatment (also activating a Gαq-coupled receptor) was completely insensitive to the pertussis toxin. Thus it appears that in corroboration with preceding reports there is negligible inositol phosphate turnover induced in peripheral tumor cells by GnRH. However at much higher doses there seems to be a PTX-sensitive capacity to stimulate inositol phosphate turnover presumably by the Gβγ-mediated activation of PLC-β.

Continuous treatment however of either JEG-3 or BPH-1 cells with 1 mM LPA failed to significantly attenuate the cell growth and invariably caused a slight elevation in cell number after five days of continuous treatment. Thus it appears that the ability of the GnRH-induced stimulation of either JEG-3 or BPH-1 cells is not correlated to their anti-proliferative action. We additionally assessed whether the GnRH stimulation of either JEG-3 or BPH-1 resulted in the significant activation of any other of the MAPK isoforms. Using specific antisera against the kinase active form of ERK5 (or BMK) we observed no specific activation of this form of MAPK however using antisera specifically recognising the active forms of either c-Jun N-terminal kinase (JNK) or p38 MAPK we noted that in JEG-3 cells there was a potent, yet delayed GnRH-induced activation of JNK and a similarly slow inset activation of p38 in the BPH-1 cells. The level of activation of the endogenous stress-activated protein kinases (SAPKs) was relatively small but greater than the GnRH-activated ERK levels in these cells. To further investigate the validity of the observed SAPK activation we transfected the tumour cell lines with myc-tagged JNK2 or p38α MAPK isoforms, stimulated the cells with GnRH and then immunoprecipitated with antimyc sera and western blotted the immunoprecipitates for total JNK/p38 protein and active JNK/p38. In FIG. 7 (panel a) GnRH causes a demonstrable, time-dependent and protracted activation of the immunoprecipitated JNK2. Activation of JNK2 typically only occurred after 30 minutes of GnRH I stimulation. In the BPH-1 cells the stimulation with GnRH I also resulted in a protracted activation of the immunoprecipitated myc-p38α. As with the activation of the JNK in the JEG-3 cells there was a considerable delay in the onset of the p38 activation unlike the ERK signalling events that typically occur and peak within 20 minutes of GnRH ligand application (FIG. 7, panel b).

GnRH-Induced Activation of Stress-Activated Protein Kinase Pathways is Involved in the Induction of a Pro-Apoptotic State We investigated whether there was a connection between the capacity of GnRH to activate the SAPK pathways and the observed generation of the early signs of apoptosis, e.g. the PS transfer from the internal face of the plasma membrane envelope to the external face, thus making it reactive with the annexin-V-FITC protein conjugate. To this end we employed the SAPK inhibitor SB203580 which at low doses (1 μM) acts as a potent inhibitor of p38 SAPK activity yet at higher doses (20 μM) exerts an additional inhibitory activity upon the JNK family of SAPK proteins (Mangoura et al (2000) *J. Dev. Neurosci.* 18, 693-704). Co-incubation of JEG-3 cells with 20 μM SB203580 and GnRH I for 48 h resulted in a significant reduction in the degree of annexin-V-FITC staining of the external face of the plasma membrane (FIG. 11, panel a, 4-6 compared to 7-9). There was observed to be no significant difference in the general growth patterns and gross morphology of the cells treated with SB203580 compared to those treated with GnRH alone or those unstimulated. DMSO vehicle controls were performed for the SB203580 treatment yet these demonstrated no significant effect upon cell growth or morphology (data not shown). In parallel experiments, but using a lower more specific dose of SB203580 (1 μM) BPH-1 cells were co-incubated with GnRH I with or without SB203580 for 48 h. As demonstrated in FIG. 11, panel b, images 4-6, there was a significant induction of annexin-V-FITC reactivity on the outer plasma membrane envelope that was almost completely abrogated by the co-treatment of GnRH I plus 1 μM SB203580. As with the experiments upon JEG-3 cells there was no significant observable change in cell morphology or growth rates either with the SB203580-treated cells or the DMSO vehicle-treated cells. Thus it appears that the inhibition of the GnRH-induced SAPK pathways in the JEG-3 cells and BPH-1 cells can attenuate the capacity of GnRHR activation to inhibit cellular proliferation in these two cell lines.

GnRH Ligand Activation of the SAPK Pathways in JEG-3 and BPH-1 Cells Occurs Via a Gαi-Based Receptor Mechanism We have demonstrated that in both the tumour cell line, JEG-3 and the hyperplastic cell line, BPH-1, that upon Type I GnRHR activation there is a profound activation of SAPK pathways and that these protein kinases are linked to the generation of the early signs of programmed cell death in both models. It has been shown by many experimental groups that the G protein coupling GnRH receptors expressed in peripheral tumour tissues is aberrant compared to that in the pituitary setting. In the pituitary the primary G protein coupling event of the stimulated GnRHR is via the Gαq-type G proteins leading to the increase in intracellular $Ca^{2+}$ and the eventual activation of protein kinase C isoforms. However in contrast in peripheral tissues the primary GnRHR G protein coupling event appears to be via the pertussis toxin-sensitive Gαi G protein pathway. This occurs despite the fact that in these cell lines there is demonstrably only one form of the GnRH receptor, i.e. the Type I GnRHR. Thus we tested whether in our experimental paradigms that GnRH ligand activation of the cells resulted in the stimulation of the SAPK pathways previously implicated in the generation of the early signs of apoptosis through a Gαi type G protein pathway. In addition we were interested in elucidating whether there was any correlation between the GnRH I-like anti-proliferative capacity of some GnRH-based peptide antagonists (Ant135-25) and their ability stimulate such atypical Gαi G protein pathways.

We first demonstrated that there was actual activation of Gαi protein in both cell lines upon GnRH and Ant 135-25 stimulation. Thus we noted that when cyclic adenosine monophosphate levels (cAMP) were measured using a commercially available fluorescent assay system (Biomol) the ability of forskolin (1 μM in JEG-3 and 3 μM in BPH-1, sufficient to give a 50% $R_{max}$ response in each case) was blunted with extended cellular pre-treatment times (10 to 60 minutes) with either 100 nM GnRH I or Ant 135-25 (FIG. 9, panel a-BPH, panel b-JEG). In FIG. 9 panels c (BPH) and d (JEG) the ability of the 60 minute GnRH I or Ant 135-25 pre-treatments to inhibit the forskolin-mediated cAMP accumulation was attenuated by a 16 h pre-treatment with 200 ng/ml PTX. Therefore it appears that both ligands can efficiently activate the adenylate cyclase inhibitory activity of Gαi in both cell models tested.

The ability of either GnRH I or Ant135-25 to stimulate the SAPK pathways in JEG-3 or BPH-1 cells was estimated and whether this SAPK pathway activation was via an atypical Gαi-type G protein pathway. Hence employing the transfected myc-JNK2 in JEG-3 cells or myc-p38α in BPH-1 cells the degree of JNK or p38 stimulation by Ant135-25 was assessed. As demonstrated in FIG. 10 (panels a and d) representative western blots show that upon both GnRH I (100 nM, 30 minutes) or Ant135-25 (100 nM, 30 minutes) stimulation there is a similar level of JNK2 or p38α activation in JEG-3 and BPH-1 cells respectively. With a pre-incubation of 16 h with 200 ng/ml of pertussis toxin (PTX) there was observed to be a significant inhibition of either GnRH I or Ant 135-25 to activate the SAPK pathways suggesting that indeed both ligands are activating Gαi-type G protein pathways. Panels b and c in FIG. 10 demonstrate the mean data compiled in JEG-3 cells for the inhibitory action of PTX pre-treatment upon GnRH I- or Ant135-25-induced JNK2 activation. Panels e and f show similar data gathered from p38α activation experiments performed in BPH-1 cells again showing that the GnRH I and Ant135-25 stimulation of p38α occurs through a Gαi PTX-sensitive pathway.

Antagonist 135-25 and not Antagonist 135-18 Potently Stimulates the Activation of SAPK Pathways in JEG-3 and BPH-1 Cells We have demonstrated that upon continuous stimulation with either GnRH I or Ant135-25 that both JEG-3 and BPH-1 cells slow down in their growth rates and demonstrate signs of an early apoptotic state. However when these experiments were performed in parallel using an agent chemically related to Ant135-25, i.e. Ant 135-18, the anti-proliferative effect seen with this agent was minimal despite its similar structure to the more potent Ant135-25. Therefore we investigated whether this phenomenon of the low anti-proliferative potency of Ant135-18 resided in its capacity to activate the Gαi-SAPK pathways. When tested for its capacity to activate either JNK2 in JEG-3 cells or p38α in BPH-1 cells Ant135-18 demonstrated a dramatically lower efficacy than GnRH I or Ant 135-25 with respect to activating the SAPK isoforms (FIG. 8). Therefore it appears that Ant135-25 like GnRH I can adequately activate the Gαi-type pathway in JEG-3 or BPH-1 cells while the chemically related Ant135-18 has a much lower potency with respect to this form of atypical GnRH receptor activation. Therefore we would suggest that this inability of Ant135-18 to induce a productive coupling between the GnRHR and the Gαi G protein pathway in these model cells lies at the centre of its poor anti-proliferative potency.

Antagonist 135-25 Demonstrates a Selective GnRH Receptor Activation Profile

We have demonstrated that despite a high degree of similarity between Ant135-18 and Ant135-25 there is a significant difference in their capacity to stimulate certain forms of GnRH receptor activity, hence the generation of an anti-proliferative effect upon three both tumorous and hyperplastic cell lines. Recent reports have suggested that the atypical GnRH receptor pharmacology observed in peripheral reproductive tumor lines is due to the expression of a Type II human GnRH receptor similar to that originally cloned by Millar et al (2001) *Proc. Natl. Acad. Sci. USA* 98, 9636-9641. We have previously shown that upon mammalian Type II (marmoset) and non-mammalian GnRH receptors that classical GnRH Type I receptor antagonists possess varying degrees of partial agonistic activity. However if indeed the peripheral anti-proliferative actions of GnRH and related ligands upon the model cells used in this present study then one would expect that Ant135-18 would possess a much greater anti-proliferative efficacy than Ant135-25 as the former displays a much greater partial agonist activity upon non-mammalian (data not shown) and mammalian Type II GnRH receptors (FIG. 12). Thus when compared in HEK293 cells expression the rat Type I GnRH receptor (SCL60) both antagonists Ant135-18 and Ant135-25 exert a classical antagonist activity and demonstrate no partial agonistic activity (FIG. 12, panels a and b). However when the two antagonists are compared in a cellular background expressing solely the marmoset Type II, i.e. αT4 gonadotropes stably expressing the marmoset Type II GnRH receptor (Millar et al (2001) *Proc. Natl. Acad. Sci. USA* 98, 9636-9641), Ant 135-18 demonstrated considerable partial agonistic activity (FIG. 12 panel c) while Ant135-25 showed no partial activity at all upon the Type II marmoset GnRH receptor (FIG. 12, panel d). Therefore it is extremely unlikely from a pharmacological and molecular biological viewpoint that the anti-proliferative actions of GnRH I or Ant135-25 are occurring via stimulation of a novel human Type II GnRH receptor.

The ability of the four major agents under study at activating ectopically expressed Type I or Type II GnRHR were tested (FIG. 12). The classical signal transduction cascade activated by GnRHR stimulation is the Gαq-PLC-β cascade. Both Type I and II receptor can stimulate the Gαq-PLC type-G-protein and activate PLC-β which cleaves phosphatidylinositol bisphosphate ($PIP_2$) into inositol tris-phosphate ($IP_3$), other lower inositol phosphates ($IP_n$) and diacylglycerol (DAG). The major function of $IP_3$ is to elevate intracellular $Ca^{2+}$ while DAG causes the activation of specific PKC (protein kinase C) isoforms. Measuring the generation of these $IP_n$s, we demonstrated that both Type I and Type II GnRHRs were activated by the endogenous ligands (Type I and II GnRH). However, only the Type II receptor was activated by 135-18 with no activation of the PLC-β signal at the Type I receptor evident (data not shown). In contrast the chemically-similar agent 135-25 exhibited no $IP_n$-generating capacity at either ectopically expressed Type I or II GnRHRs (FIG. 12).

Panels a and b of FIG. 12 depict the generation of free cytoplasmic $^3H$-myo-inositols on the plasma membranes of HEK293 cells expressing the Type I GnRHR and of αT4 gonadotropes expressing the marmoset Type II GnRHR. Prior to agonist stimulation the respective cells were incubated in inositol-free growth media supplemented with 1 μ Ci/ml $^3H$-myoinositol for 48 h. G protein coupled receptor (GPCR)-induced activation of PLC-β results in the cleavage of $PIP_2$ (incorporating tritium $^3H$) into free lower inositol phosphates ($IP_n$s). Stimulation of the Type I or Type II GnRHRs with GnRH I or GnRH II respectively yields an increase in free tritiated inositol phosphates. However stimulating either receptor with antagonist 135-25 (10 μM-1 μ M) failed to generate significant free inositol phosphate. Therefore it appears that the 135-25 antagonist is specifically unable to activate Gαq-type G-proteins despite displaying a high binding affinity for both Type I and II GnRHRs (data not shown) and a high anti-proliferative efficacy.

Therefore it appears that 135-25 possesses the potential to attenuate tumour cell proliferation without having any significant effect upon other GnRHR signalling modalities. As the two antagonists 135-25 and 135-18 employed differ only slightly in their chemical composition (i.e. a MePal residue in position 5 for 135-25 of a Ile for 135-18), yet have different efficiencies against tumour cell proliferation their physio-chemical differences may indicate a valuable target for modification at this site to enhance the compounds anti-tumour capacity of GnRH ligands.

Discussion

In this current study we have demonstrated that like endogenous GnRH ligands such as GnRH I, typically described 'antagonists' can act as agonists with respect to peripheral tumor cells due to the altered pharmacological profile of the receptor in these cells. The demonstration of the elevated potency of Ant 135-25 over Ant 135-18 with respect to the antiproliferative effect appeared to due to the relative abilities of the two peptides to stabilize an active form of the receptor able to couple productively to Gαi. Thus the designation of Ant 135-25 as a GnRH receptor 'antagonist' is somewhat spurious as this only describes its ability to activate/stabilize the Gαq-preferring form/state of the Type I GnRH receptor. Hence we have described in essence that Ant 135-25 exerts a potent antiproliferative action due to its selective ability to activate a Gαi-coupling form of the Type I GnRH receptor while being unproductive upon Gαq-coupling forms of the receptor.

Initial hypotheses concerning the nature of the divergence in signalling between GnRH-responsive sites in the pituitary and those in peripheral reproductive tissues suggested that the receptor present in these peripheral sites was of a distinct nature those in the gonadotrope. However recent evidence has suggested that the two receptor sites are indeed the same, yet their associated signal transduction mechanisms are clearly distinct (Chegini et al (1996) *J. Clin. Endocrinol. Metab.* 81, 3215-3221; Yin et al (1998) *Life Sci.* 62, 2015-2023; Chatzaki et al (1996) *Cancer Res.* 56, 2055-2065).

This dichotomy also extended to the effects of agonist and antagonists of the pituitary form of GnRH signalling as proliferation of both endometrial and ovarian cancer cells can be inhibited by agonistic and antagonistic analogues of GnRH (Emons et al (1997) *Trends Endocrinol. Metab.* 8, 335-362). A solution to this problem was proposed by Imai et al ((1996) *J. Clin. Endocrinol. Metab.* 77, 132-137) in which they speculated that the G protein ai that possibly couples the GnRH receptor to the effector may be responsible for the differences in response between peripheral tumors and the anterior pituitary. Interestingly it has been shown that, as with our study, functional LPA-mediated G$\alpha$q-coupling activity is present in these tumor cells (Grundker et al (2001) *Endocrinology* 142, 2369-2380), thus a pathophysiological loss of G protein cannot explain the paradoxical change in receptor signalling. In the present study little GnRH-mediated activation of G$\alpha$q was observed but other groups have recently demonstrated that in other reproductive tumor lines such as Ishikawa cells, GnRH can induce coupling to G$\alpha$q (Grundker et al (2001) *Endocrinology* 142, 2369-2380). However this group found that this extant G$\alpha$q signalling was not involved in the generation of the antiproliferative effect of GnRH. Thus it is probable that the functional signalling complexes containing the GnRH receptors in peripheral tumor sites are able to coerce the receptor into specific G$\alpha$i coupling and those complexes in the pituitary are not. Whatever the protein intermediates responsible for this shift in functionality it is clear that additional receptor-interacting factors can dramatically alter the way in which a given ligand can direct its signal to the intracellular environment and with clearly distinct physical endpoints. This differential coupling of the receptor therefore necessitates us to re-evaluate our terminology with respect to the nature of the ligands interaction with the GnRH receptor at these peripheral tumor sites. Thus we have shown that while Ant 135-25 can be adequately described as an antagonist at the anterior pituitary level with respect to the activation of the G$\alpha$q-based signalling mechanisms it behaves as a true agonist in the peripheral cells as it appears almost equally effective at stimulating the existing G$\alpha$i-coupled Type I GnRH receptors. In addition we have clearly demonstrated that a separation between these two effects at the periphery and the pituitary can be engineered by alteration of the primary sequence of the GnRH receptor peptide ligand. Therefore conversion of the single amino acid difference between Ant 135-18 and Ant135-25 resulted in a dramatic elevation of the agent's potency at the G$\alpha$i-coupled peripheral GnRH receptor while not changing its ability to functionally inhibit the action of GnRH at the pituitary G$\alpha$q-coupled receptor.

The use of GnRH analogues, both agonist and antagonists, is now widely accepted with applications in gynaecology, reproductive medicine and oncology. The mechanisms of action of the majority of these therapeutics is based on an inhibition of the anterior pituitary and the gonads. Classical 'antagonistic' GnRH receptor ligands have an advantage over GnRH agonistic peptides due to the fact that they inhibit the secretion of gonadotropins and sex steroids immediately after first application achieving more rapid therapeutic effects than GnRH agonists that require repeated administration (Schally, A. V. (1999) *Peptides* 20, 1247-1262). The repeated exposure to agonistic agents is required as they need to induce a functional downregulation of the anterior pituitary GnRH signalling system. For conditions such as prostate cancer GnRH classical 'antagonist' molecules are preferable to agonists specifically as they avoid the so-called 'flare' of the disorder which occurs in approximately 10-20% of patients when agonists are given as single agents (Schally, A. V. & Comaru-Schally, A. M. (1997) Hypothalamic and other peptide hormones. In: Holland J. F., Frei, E., Bast, R. C., Kufe, D. E., Morton, D. L., Weichselbaum, R. R., eds. *Cancer Medicine*, 4$^{th}$ Ed. Baltimore: Williams & Wilkins p1067-1086.). Pre-existing antagonistic therapies for reproductive tumors involve the administration of Cetrorelix which has been demonstrated in some circumstances to attenuate the growth of androgen-dependent prostate cancers (Redding et al (1992) *Cancer Res.* 52, 2538-2544; Korkut et al (1991) *Proc. Natl. Acad. Sci., USA* 88, 884-888). However considerably higher doses of Cetrorelix were required to attenuate the growth of androgen-resistant tumor cells (Jungwirth et al (1987) *Prostate* 32, 164-172; Jungwirth et al (1997) *Eur. J. Cancer* 33, 1141-1148) suggesting that its direct antiproliferative efficacy could be significantly lower than its ability to attenuate anterior pituitary gonadoptropin release which would deprive the androgen-sensitive tumor of its growth-sustaining steroid. Thus it appears that the capacity to directly attenuate tumor growth may be specifically desirable to agents aimed at relieving aggressive androgen-insensitive prostate tumors, hence our attempts at elevating the direct antiproliferative potency of the antagonistic agent Ant 135-25. Indeed in our hands Cetrorelix was significantly less potent than Ant 135-25 when compared in their abilities at stimulating PTX-sensitive/G$\alpha$i-dependent MAPK isoform activation (data not shown). In addition it appears that Cetrorelix may not possess a true and profound antiproliferative effect upon all reproductive tumors expressing GnRH receptors, e.g. the antiproliferative effect of triptorelin (GnRH agonist) upon LNCaP prostate cells was efficiently inhibited in the presence of Cetrorelix (Ravenna et al (2000) *J. Androl.* 21, 549-557). Thus it is possible that Cetrorelix has a significantly lower antiproliferative potency than Triptorelin and therefore in its presence acts as a functional antagonist of its action. In other experimental paradigms other classical GnRH antagonists, e.g. Antide, have been shown to functionally inhibit the antiproliferative effects of classical GnRH receptor agonists (Kang et al (2000) *Endocrinology* 141, 72-80). Thus it is possible that the majority of existing therapeutics do not have a significantly potent direct anti-tumor effect, which would be desirable for steroid-resistant neoplasms. Their poor potency may be due to their low potency with respect to stabilizing/inducing the G$\alpha$i-preferring conformation/state of the Type I GnRH receptor. We have therefore shown that by modifying an antagonist with a low direct antiproliferative potency (Ant 135-18) by one residue we have significantly elevated its antiproliferative potency by allowing it to potently activate the G$\alpha$i-type of GnRH signalling seen in peripheral reproductive tumors. An agent such as Ant135-15 is believed to display several properties making it superior to current GnRH-based peptide treatment of reproductive neoplasms, i.e. not being an agonist there is no initial disease 'flare-up' (Schally, A. V. & Comaru-Schally, A. M. (1997) Hypothalamic and other peptide hormones. In: Holland J. F., Frei, E., Bast, R. C., Kufe, D. E., Morton, D. L., Weichselbaum, R. R., eds. *Cancer Medicine*, 4$^{th}$ Ed. Baltimore: Williams & Wilkins p1067-1086.), its inhibitory action at the pituitary will decrease serum levels of sex steroids thereby attenuating steroid-sensitive neoplasm growth and finally its enhanced direct anti-tumor effect would be directly cytotoxic to steroid-resistant cells potentially present in the neoplasm.

EXAMPLE 2

Treatment of Breast Cancer

A patient presenting with breast cancer is administered from 1 to 100 mg of the compound Ant 135-25 intravenously daily for a week.

EXAMPLE 3

Treatment of Benign Prostastatic Hyperplasia (BPH)

A patient presenting with BPH is administered from 1 to 100 mg of the compound Ant 135-25 intravenously daily for a week.

EXAMPLE 4

Treatment of Prostate Cancer

A patient presenting with prostate cancer is administered a depot for the delivery of the compound Ant 135-25.

The invention claimed is:
1. A method of combating tumors or reproductive tissue hyperplasia in a patient, the method comprising administering the compound Ac-D-Nal(2)-D-4-ClPhe-D-Pal-Ser-1 MePal-D-IsopropylLys-Leu-lsopropylLys-Pro-D-AlaNH$_2$.
2. A method according to claim) 1 wherein the tumor is a sex-hormone dependent cancer.
3. A method according to claim 1 wherein the tumor is a prostate tumor.
4. A method according to claim 1 wherein the reproductive tissue hyperplasia is benign prostate hyperplasia or uterine fibroids.

* * * * *

UNITED STATES PATENT AND TRADEMARK OFFICE
CERTIFICATE OF CORRECTION

PATENT NO.       : 7,361,633 B2                              Page 1 of 1
APPLICATION NO.  : 10/494989
DATED            : April 22, 2008
INVENTOR(S)      : Maudsley et al.

It is certified that error appears in the above-identified patent and that said Letters Patent is hereby corrected as shown below:

Claim 2, line 1, delete "claim ) 1" and insert in its place --claim 1--.

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

PATENT NO.         : 7,361,633 B2
APPLICATION NO.    : 10/494989
DATED              : April 22, 2008
INVENTOR(S)        : Maudsley et al.

Page 1 of 1

It is certified that error appears in the above-identified patent and that said Letters Patent is hereby corrected as shown below:

Column 26, Claim 2, line 13, delete "claim ) 1" and insert in its place --claim 1--.

This certificate supersedes the Certificate of Correction issued August 19, 2008.

Signed and Sealed this

Sixteenth Day of September, 2008

JON W. DUDAS
*Director of the United States Patent and Trademark Office*